(12) United States Patent
Sinden et al.

(10) Patent No.: US 7,048,921 B2
(45) Date of Patent: *May 23, 2006

(54) NEURAL TRANSPLANTATION USING PLURIPOTENT NEUROEPITHELIAL CELLS

(75) Inventors: John Sinden, London (GB); Jeffrey A. Gray, London (GB); Helen Hodges, London (GB); Timothy Kershaw, London (GB); Fiza Rashid-Doubell, Oxford (GB)

(73) Assignee: ReNeuron Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,274

(22) Filed: Jan. 12, 2001

(65) Prior Publication Data

US 2001/0001662 A1    May 24, 2001

Related U.S. Application Data

(63) Continuation of application No. 09/672,606, filed on Sep. 28, 2000, now abandoned, which is a continuation of application No. 09/043,061, filed as application No. PCT/GB96/02251 on Sep. 12, 1996, now abandoned.

(30) Foreign Application Priority Data

Sep. 12, 1995  (GB) .................. 9518606.0

(51) Int. Cl.
  *A61K 35/00* (2006.01)
  *C12N 15/63* (2006.01)
(52) U.S. Cl. .................... 424/93.21; 435/325
(58) Field of Classification Search ......... 424/93.1, 424/93.21, 93.2; 435/325
See application file for complete search history.

(56) References Cited

U.S. PATENT DOCUMENTS

| 5,270,191 | A |   | 12/1993 | McKay et al. |
| 5,580,777 | A | * | 12/1996 | Bernard et al. |
| 5,690,927 | A |   | 11/1997 | Major et al. |
| 5,753,491 | A |   | 5/1998  | Major et al. |
| 5,817,773 | A |   | 10/1998 | Wilson et al. |
| 5,851,832 | A |   | 12/1998 | Weiss et al. |
| 5,958,767 | A |   | 9/1999  | Snyder et al. |
| 6,197,585 | B1 |  | 3/2001  | Stringer |
| 6,200,806 | B1 |  | 3/2001  | Thomson |
| 6,399,384 | B1 |  | 6/2002  | Jat |
| 6,528,306 | B1 |  | 3/2003  | Snyder et al. |
| 6,569,421 | B1 | * | 5/2003  | Hodges ............ 424/93.2 |

| 2002/0123143 | A1 | 9/2002 | Toma et al. |
| 2003/0147873 | A1 | 8/2003 | Sinden et al. |

FOREIGN PATENT DOCUMENTS

| GB | WO 97/10329  | * | 3/1997  |
| WO | WO 89/09816 A1 |   | 10/1989 |
| WO | WO 92/11355 A1 |   | 7/1992  |
| WO | WO 93/18137 A1 |   | 9/1993  |
| WO | WO 98/07841 A1 |   | 2/1998  |
| WO | WO 00/50568 A3 |   | 8/2000  |

OTHER PUBLICATIONS

Netto et al. Foetal grafts from hippocampal regio superior alleviate ischaemie-induced behavioral deficits** pp. 107-112 1993.*
Sinden et al. Recovery of spatial learning by grafts of a conditionally jimmortalized hippocampal neuroepithelial cell line into the ischaemia-lesioned hippocampus pp. 599-608 vol. 91 No. 3 1997.*
Sanberg et al. Cellular therapeutic approaches for neurodegenrative disorders pp. 139-142 2998.*
Sicheffler et al. Marrow-mindedness: a perspective on neuropoiesis 1999 22, pp. 348-357.*
Hodges et al. Cognitive deficits induced by global cerebral ischaemia: Prospects for transplant therapy pp. 763-780 1997.*
Rashid-Doubell et al. Effects of basic fibroblast growth factor and gamma interferon on hippocampal progenitor cells derived from the H-2Kb-tsA58 transgenic mouse p. S63 (no date).*
Renfranz et al., 1991, Cell, vol. 66, p. 713-729.*
White et al., 1992, J. Chem. Neuroanatomy, vol. 5, p. 327-330.*
Villa, 2000, Exp. Neurol., vol. 161, p. 67-84.*
Gray, Aug. 29, 1999, Philosophical Transactions of the Royal Soc. London, vol. 354, No. 1388. p. 1407-1421.*
Snyder, Evan Y., David L. Deitcher, Christopher Walsh, Susan Arnold-Aldea, Erika A. Hartwieg, Constance L. Cepko (Jan. 10, 1992) "Multipotent Neural Cell Lines Can Engraft and Participate in Development of Mouse Cerebellum" *Cell* 68:33-51.

(Continued)

*Primary Examiner*—Michael C. Wilson
(74) *Attorney, Agent, or Firm*—Saliwanchik, Lloyd & Saliwanchik

(57) ABSTRACT

The subject invention pertains to a novel method of correction of behavioral and/or psychological deficits made possible by the intracerebral transplantation of pluripotent neuroepithelial cells. Cells, cell lines, pharmaceutical preparations, medicaments, methods for the production and maintenance of the cell lines for use in the method of the invention are encompassed by the invention.

17 Claims, 20 Drawing Sheets

OTHER PUBLICATIONS

Figure 1:
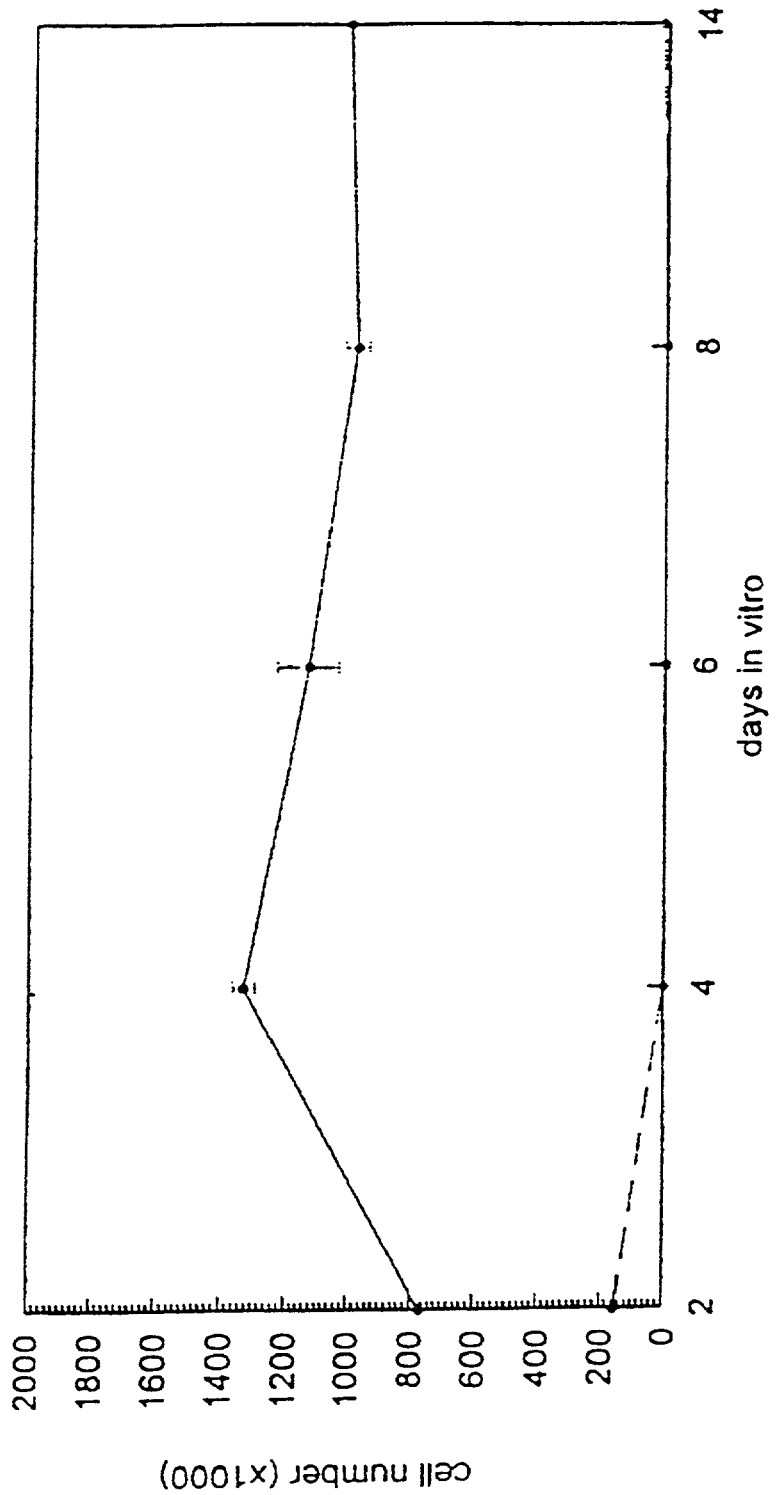

Snyder, Evan Y. and John H. Wolfe (1996) "Central nervous system cell transplantation: a novel therapy for storage diseases?" *Curr. Opin. Neurol.* 9:126-136.

Snyder, Evan Y., Cliff Yoon, Jonathan D. Flax, Jeffrey D. Macklis (Oct. 14, 1997) "Multipotent neural precursors can differentiate toward replacement of neurons undergoing targeted apoptotic degeneration in adult mouse neocortex" *Proc. Natl. Acad. Sci.* 94(21):11663-11668.

Virley, David, Rosalind M. Ridley, John D. Sinden et al. (1999) "Primary CA1 and conditionally immortal MHP36 cell grafts restore conditional discrimination learning and recall in marmosets after excitotoxic lesions of the hippocampal CA1 field" *Brain* 122(2321-2335.

Whittemore, S. R. et al. "Isolation and characterization of conditionally immortalized astrocyte cell lines derived from adult human spinal cord" *Glia*, Mar. 1994, 10:221-226.

Anderson, W.F. "Human gene therapy" *Nature*, 1998, 392:25-30.

Allay, J.A. et al. "LacZ and interleukin-3 expression *in vivo* after retroviral transduction of marrow-derived human osteogenic mesenchymal progenitors" *Human Gene Therapy*, 1997, 8:1417-1427.

Chopp, M. et al. "Adult bone marrow transplantation for treatment of stroke in adult mice" *Society for Neuroscience*, 1999, 25:1309, abstract No. 528.2 (abstract).

Cepko, C.L. "Immortalization of neural cells via retrovirus-mediated oncogene transduction" *Ann. Rev. Neurosci.,* 1989, 12:47-65.

Frederiksen, K. et al. "Immortalization of Precursor Cells from the Mammalian CNS" *Neuron*, 1988, 1:439-448.

Jat, P.S. "Direct derivation of conditionally immortal cell lines from an $H-2K^b$ -tsA58 transgenic mouse" *Proc. Natl. Acad. Sci. USA*, 1991, 88:5096-5100.

Major, E.O. et al. "Establishment of a line of human fetal glial cells that supports JC virus multiplication" *Proc. Natl. Acad. Sci. USA*, 1985, 82:1257-1261.

Mezey, E. and K.J. Chandross "Bone marrow: a possible alternative source of cells in the adult nervous system" *Euro. J. Pharmacology*, 2000, 405:297-302.

Palu, G. et al. "In pursuit of new developments for gene therapy of human diseases" *J. Biotechnology*, 1999, 68:1-13.

Wyllie, F.S. et al. "A phenotypically and karyotypically stable human thyroid epithelial line conditionally immortalized by SV40 large T antigen" *Cancer Res.,* 1992, 52:2938-2945.

Stem Cells: Scientific Progress and Future Research Directions, Jun. 2001, Introductory Chapter and Chapters 8 and 11.

* cited by examiner

NEURAL TRANSPLANTATION USING PLURIPOTENT NEUROEPITHELIAL CELLS

This application is a continuation application of U.S. Ser. No. 09/672,606, filed Sep. 28, 2000 now abandoned; which is a continuation application of U.S. Ser. No. 09/043,061, filed Mar. 12, 1998, now abandoned; which is a national stage application of PCT/GB96/02251, filed Sep. 12, 1996, published as WO 97/10329 on Mar. 20, 1997.

The present application relates to the correction of behavioural and/or psychological deficits by the intracerebral transplantation of neural cells, and to cells and medicaments therefor. The invention also concerns methods for the production and maintenance of the cell lines.

Behavioural and/or psychological deficits are caused by many diseases and may also be caused when the brain undergoes trauma. For example, motor dysfunction is one symptom of Parkinson's disease. As yet, in most cases, there is no satisfactory treatment available.

The present invention provides for a method of treatment of a behavioural and/or psychological deficit which comprises intracerebral transplantation of a therapeutically effective amount of pluripotent neuroepithelial cells.

The present invention is based in part on the observation that, when transplanted into a damaged or diseased brain, pluripotent neuroepithelial cells appear to respond to signals from the damaged or diseased brain by taking up a phenotype that is able to replace or compensate for functional deficits to which the damage or disease otherwise leads.

The term "pluripotent" is used herein to denote a an undifferentiated neuroepithelial cell that has the potential to differentiate into different types or different phenotypes of cell, in particular into cells having the appropriate phenotype for the intended use. The cell type or phenotype into which such a pluripotent cell finally differentiates is at least partly dependent on the conditions in which the cell exists or finds itself.

For use in the present invention the neuroepithelial cells should be capable of differentiating into cells appropriate to repair or compensate for damage or disease in the target area of the brain. It will be appreciated that cells for transplantation need not be capable of differentiation into all types or phenotypes of neural cells. The cells may, for example, be bipotent. However, a high degree of potency is generally preferred as this gives greater flexibility and potential for transplantation into different areas of the brain.

Suitable pluripotent cells include those called or known as "stem cells" and those called or known as "precursor cells".

The pluripotent neuroepithelial cells are advantageously, and will generally be, conditionally immortal.

The treatment may be carried out on any mammal but the present invention is especially concerned with the treatment of humans, especially treatment with human cells, and with human cells and cell lines.

The present invention provides a mammal which has undergone treatment according to the present invention.

The present invention provides isolated human, pluripotent neuroepithelial cells.

The present invention especially provides human, conditionally immortal pluripotent neuroepithelial cells.

The present invention further provides a conditionally immortal, pluripotent, neuroepithelial cell line, especially for therapeutic use, more especially for the treatment of a behavioural and/or psychological deficit.

The cells of the present invention are capable of correcting a behavioural or psychological deficit when implanted into a damaged part of the human brain. The term "damage" used herein includes reduction or loss of function. Damage may be caused by any of a variety of means including physical trauma, hypoxia (lack of oxygen), chemical agents, for example, damage may be caused by drug abuse, and disease. The following diseases and pathological conditions are examples of diseases or conditions which result in behavioural and/or psychological deficits which may be treated in accordance with the present invention: traumatic brain injury, stroke, perinatal ischaemia, including cerebral palsy, Alzheimer's, Pick's and related dementing neurodegenerative diseases, multi-infarct dementia, Parkinson's and Parkinson's type diseases, Huntington's disease, Korsakoff's disease and Creuzfeld-Jacob disease. Amnesia, particularly following transitory global ischaemia such as after cardiac arrest or coronary bypass surgery, may also be treated in accordance with the present invention.

The present invention further provides a process for the production of human, conditionally immortal, pluripotent, neuroepithelial cells which comprises the steps of:
(a) obtaining neuroepithelial cells from a human fetus, the cells being at a stage early enough in the developmental pathway that they have the ability to differentiate into a variety of different brain cell types,
(b) introducing into those cells DNA which comprises a sequence capable of causing the cells to be conditionally immortal under the control of appropriate control elements, and
(c) maintaining the cells in vitro under permissive conditions.

The process may further include the step of cloning the cells to obtain one or more cell lines.

A further aspect of the invention provides for pluripotent, neuroepithelial cells, optionally in isolated form, for therapeutic use, especially in humans. The therapeutic use may be treatment of a behavioural and/or psychological deficit.

A further aspect of the invention provides for conditionally immortal, pluripotent, neuroepithelial cells for therapeutic use, especially in humans. The therapeutic use may be treatment of a behavioural and/or psychological deficit.

The present invention further provides for the use of pluripotent, neuroepithelial cells, optionally in isolated form, in the manufacture of a medicament for the treatment of a behavioural and/or psychological deficit. The medicament to be administered comprises pluripotent neuroepithelial cells.

The present invention especially provides for the use of conditionally immortal, pluripotent, neuroepithelial cells in the manufacture of a medicament for the treatment of a behavioural and/or psychological deficit. The medicament to be administered comprises conditionally immortal, pluripotent, neuroepithelial cells.

The conditionally immortal cells according to, and used in, the present invention may be from clonal cell lines or may be of mixed population. Cells from clonal cell lines may be preferred. Cells from a single cell line may be used or a mixture of cells from two or more cell lines may be used.

The invention further provides a pharmaceutical preparation comprising cells according to the invention and a pharmaceutically acceptable carrier.

Transplantation of conspecific fetal neural tissue into a damaged brain has been studied in animal experiments and consequent repair has been observed at the neuroanatomical, physiological and behavioural levels (Dunnett & Bjorklund, 1994). There has been some application of this work in the treatment of the motor dysfunction of Parkinson's disease (Lindvall, 1994) but widespread use of this technique is handicapped by the need for tissue derived from conspecific fetal brain. The fetal tissue required must be specific to the type of damage one aims to repair and it must be taken at a precise, time-limited stage during brain development that differs according to both brain region and cell type. This leads to both practical and ethical problems.

Work on fetal tissue transplant (Sinden, 1995) in certain types of damage has shown that very specific matching of cell types is required to obtain improvement in cognitive function.

We have found that when conditionally immortal pluripotent neuroepithelial cells are implanted into a damaged brain the cells differentiate into the correct form of cell required to repair the damage and the differentiated cells are able to form the appropriate connections required to improve function. The phenotype of the differentiated cells may be the same as the phenotype of the damaged or lost cells, however, the differentiated cells may be of a different phenotype, or of a number of phenotypes. In any case, the cells take up a phenotype that is capable of functionally integrating and compensating for the damaged or lost cells. That is assisted by the propensity, that we have discovered, of the cells to migrate to, and seek out, damaged tissue.

The use of pluripotent cells means that with one clonal cell line it is possible to repair damage in number of different areas of the brain. It also means that if more than one particular cell type is required to repair damage in a given area then a single pluripotent cell line will be capable of differentiating into the different types of cells required.

Conditionally immortal cells are cells which are immortal under certain permissive conditions but are not immortal under nonpermissive conditions. In the present case this means that by conditionally immortalising pluripotent precursor cells extracted from fetal tissue and maintaining them under permissive conditions the development of the precursor cells may be arrested at a chosen stage and they may be propagated for long periods. Use of conditionally immortalisation allows the development of clonal lines which are readily expandable in vitro. If the conditions under which the cells are maintained are switched to nonpermissive conditions, the development of the cells is allowed to continue. If the correct conditions are provided the cells will continue to develop and will differentiate.

Immortalised cells are usually prepared by the transduction of an oncogene into cells. There is therefore a risk of tumour formation in the long term, so such cells are not preferred for use in the present invention.

Conditionally immortal cells have the advantages of immortal cells in that they are "frozen" in the desired stage of development, are easily maintained and multiply well when under permissive conditions but they may be used in transplants as long as the environment into which they are transplanted has nonpermissive conditions. In the case of the cells of the present invention the gene used to confer conditional immortality should be chosen so that the conditions present in the brain will correspond to nonpermissive conditions.

The usual way to immortalise the cells is by transduction of an oncogene. The use of conditionally immortal cells means that under nonpermissive conditions the cells do not have oncogenic properties and so this excludes any possibility of the implantation of cells leading to tumour growth.

If non-immortal cells are used then these may be maintained in vitro in culture media with the addition of growth factors.

The gene which is used to confer conditional immortality may be incorporated into cells after extraction from a fetal animal. Alternatively, transgenic animals, other than humans, whose neural epithelial cells comprise a gene for conferring conditional immortality may be prepared and bred. If transgenic animals are bred then the cells collected from the fetal animal tissue are already conditionally immortal and do not require further treatment.

The cells used in the treatment of humans should preferably be derived from human cells to reduce problems with immune rejection. This requires the use of fetal tissue. The use of conditionally immortal cells means that once a population of cells has been established it is not necessary to use fetal tissue again. For example, cells are taken from a human fetus at the appropriate stage of development and the DNA necessary to cause conditional immortality in the cells is inserted. Those cells may then be propagated or they may be cloned and individual cell lines selected. Maintenance of the mixed populations and/or of selected cell lines provides a constant source of material for implantation.

To treat a patient it is generally of assistance to know where damage has occurred in the brain. Once the existence of damage has been established, whether it be in one isolated area or in several areas, treatment by implantation of cells into the damaged area may be carried out. In many cases, however, the location and/or type of damaged tissue may be unknown or only poorly characterised. For example, neurodegenerative diseases may lead to widespread damage to different types of cells. Treatment of such damage is still possible and is assisted by the ability of pluripotent neuroepithelial cells to migrate extensively once transplanted and to seek out damaged tissue. The pluripotent cells may be transplanted at a single site, or preferably at multiple sites, and are able to migrate to the site(s) of damage and, once there, differentiate in response to the local microenvironment, into the necessary phenotype or phenotypes to improve or restore function. Post mortem analysis of the brains of rats that had received transplants of cells of a conditionally immortal pluripotent neuroepithelial cell line showed that the cells aggregated in the area of the damaged tissue, see Example 9 below, thus illustrating the propensity of the cells to establish and integrate themselves in the area of damage rather than in an area of undamaged tissue. The pluripotent nature of the cells and their propensity for damaged tissue means that treatment with cells from a single cell line of high potency is able to lead to compensation for widespread damage of a number of different cell types.

After treatment the progress of the patient may be monitored using behavioural and/or psychological tests and/or, if desired, tests which monitor brain activity in selected areas of the brain. For example, tests for cognitive function may be performed before and after transplantation.

Preferably, treatment will substantially correct a behavioural and/or psychological deficit. However, that may not always be possible. Treatment according to the present invention and with the cells, medicaments and pharmaceutical preparations of the invention, may lead to improvement in function without complete correction. Such improvement will be worthwhile and of value.

The number of cells to be used will vary depending on the nature and extent of the damaged tissue. Typically, the number of cells used in transplantation will be in the range of about one hundred thousand to several million. Treatment need not be restricted to a single transplant. Additional transplants may be carried out to further improve function.

The present invention is illustrated by work we have carried out on rats which have brain damage. In the experiments described below conditionally immortal cells used for transplantation are derived from the H-2K$^b$-tsA58 transgenic mouse developed by M. Noble and his associates at the Ludwig Institute for Cancer Research (Jat et al., 1991). All cells from this mouse possess a temperature-sensitive oncogene (tsA58, the temperature sensitive mutant of the SV40 large T antigen under the control of the interferon-inducible H-2K$^b$ promotor) such that the cells divide at the permissive temperature (lower than body temperature, 33° C.) but differentiate only when restored to mouse body temperature (38° C.–39° C.). It is this feature that provides them with conditional immortality. This allowed us to clone and expand cell lines in vitro which then differentiated upon transplantation into a host brain. A number of cell lines were cloned from a population of cells taken originally from the transgenic mouse, specifically, from embryonic day 14 (E 14) hippocampus. We studied the rats, which received transplants of those cells, for at least 8 months and in no case did the cells, after transplantation, form tumours. Furthermore, in post-mortem histological preparations, the transplanted cells (marked by prior transfection with a lac-z reporter gene) have the appearance of differentiated cells appropriate to the rodent nervous system.

The cloned cell lines show the potential, in vitro, to differentiate into more than one phenotype, e.g., into both astroglial and neuronal phenotypes, see Example 4 below.

The lesion-and-behaviour model in which we have demonstrated that cloned cell lines are able to restore function in the damaged brain is one that we have previously studied intensively using fetal conspecific transplants (see Sinden et al., 1995). It utilises rats in which the technique for four-vessel occlusion (4 VO), simulating human heart attack, causes relatively circumscribed and specific damage to the CA 1 pyramidal cells of the dorsal hippocampus, along with a cognitive deficit manifest as difficulty in locating a submerged and invisible platform in a swimming pool. This lesion and behaviour model provides a model of cognitive dysfunction occurring as a consequence of a common form of brain damage, i.e., transient loss of blood supply to the brain, for example, as may occur during cardiac arrest.

We have previously demonstrated that, for fetal cell-suspension transplants to restore performance in this task, they must be highly specific to the damage caused by 4VO: transplants containing CA 1 pyramidal cells are effective; transplants containing cholinergic cells from the basal forebrain, granule cells from the dentate gyrus, or even a different class of pyramidal cells (CA3) from the hippocampus are ineffective. Examples 5 to 8 below described experiments in which both the clonal cell lines and a mixed population of E 14 hippocampal neuroepithelial cells taken from the H-2K$^b$-tsA58 transgenic mouse provide effective transplants for restoration of cognitive function in this model.

We have found that two of the three clonal cell lines tested, the MHP36 cell line (previously known as the C36 cell line) and the MHP3 cell line are as effective at restoring cognitive function as fetal rat transplants containing CA 1 pyramidal cells. The third cell line tested, the MHP15 cell line (previously known as the C15 cell line) leads to an improvement of function but does not show as great an improvement as MHP36 and MHP3. The chances that we happened to pick upon cell lines that would differentiate into CA 1 pyramidal cells, irrespective of the nature of the host brain environment, are small. Thus it appears that the cell lines are capable of responding to damage-associated signals so as to differentiate into cells, of one or more types, that are able to re-establish the necessary connections and restore the function(s) discharged by the damaged tissue. It is this capacity that provides both a strategy and a material basis for transplant therapies with which to target a wide range of behavioural and psychological deficits consequent upon an equally wide range of forms of damage to the human brain, while circumventing the ethical and practical problems associated with the use of human fetal tissues.

The two cell lines which have shown the greatest ability, so far, to restore function are both FGF2-responsive, i.e., they substantially increase their proliferation in both permissive and non-permissive culture in the presence of that growth factor, whereas the third cell line is only slightly responsive. Cells and cell lines which show significantly increased proliferation in response to the addition of a growth factor to their culture environment are therefore generally preferred. The cells may be tested under permissive conditions and/or nonpermissive conditions. Cells showing the greatest increase in proliferation are generally most preferred. The growth factor used to test the cells should preferably be appropriate to the area of the brain in which the cells are intended for use, i.e., a growth factor secreted in that area. For example, cells intended for the repair of tissue in the hippocampus may be tested with FGF2 (also known as bFGF). Cells responsive to FGF2 are generally preferred. Other mitogenic growth factors may be used in testing, including EGF and NGF.

The invention therefore provides a method of testing comprising maintaining a population of cells of a conditionally immortal pluripotent neuroepithelial cell line in vitro and culturing portions of the cells under permissive conditions, in the presence and absence of a growth factor, for example, FGF2, and determining the proliferation of the cells. Preferably the cells are also tested under nonpermissive conditions. Those cells which are responsive, i.e., show significantly increased proliferation in the presence of the growth factor under both permissive conditions, and preferably also under nonpermissive conditions, appear to be cells which are especially suitable for use in the treatment of the invention. The growth factor may, for example, be used at a concentration of 10 ng/ml.

The temperature-sensitive oncogene which confers conditional immortality upon cells derived from the H-2K$^b$-tsA58 transgenic mouse can be introduced into human cells in vitro. Well known techniques for the introduction of exogenous DNA exists and these may be used, for example, the gene may be introduced by transfection of the cells. Normal screening techniques for checking that the gene has been incorporated may be used, for example, Southern blotting may be used to screen for DNA insertion sites. In some cases markers may be used or, if the ts SV40 large T antigen gene is used then cells may be screened at the permissive temperature for expression of SV40 as described in Example 4.

It should be understood that although the experiments described in the Examples below have been carried out using the ts SV40 large T antigen gene to confer conditional immortality on the cells, any other gene which is capable of causing conditional immortality may be used. Such genes may be constructed from known oncogenes. For example, a conditionally immortal gene has been constructed from the c-myc oncogene and is described by Hoshimaiuaru et al, 1996.

In the experiments on rats which are described in Examples 6, 7 and 8 below conditionally immortal pluripotent cells have been used to repair a very specific type of damage. The uses of cells according to the invention are not limited to repair of that particular type of damage. Transplantation into any area of the brain is envisaged with consequent improvement in function.

The part of the fetal brain from which the neuroepithelial cells are taken and the precise time (stage and development) may vary. If pluripotent cells are desired then the cells must, however, be taken at a point early enough in the developmental pathway that they have the ability to differentiate into the desired variety of different types and/or phenotypes of brain cell types. For example, in the case of cells taken from the embryonic mouse hippocampus the cells may be taken on embryonic day 14 to 15. Human cells may be taken at the equivalent developmental stage. For example, cells may be taken from human fetuses at about 8 weeks.

Cells which have been removed may be screened in vitro to ensure that they are still able to differentiate, in particular, to differentiate into the appropriate type or phenotype of cell. Different areas of the brain when damaged may produce different signals, for example, growth factors, and/or different types of damage may cause different signals. The ability to differentiate may be determined in vitro in the presence of the appropriate signal, for example, the appropriate growth factor. Example 4 below describes a procedure in which the ability of cells to differentiate into neuronal and glial phenotypes may be shown.

Some behavioural and/or psychological deficits are caused by the absence of one or more chemicals in an otherwise healthy brain. It has previously been proposed that transplants of transgenic cells could be used to supply the missing chemicals. The present invention is not specifically concerned with such problems. Although the cells of the present invention may be genetically modified to include extra genes which express desired products, this will not usually be necessary because the cells used according to the present invention, once transplanted, differentiate and then function fully as replacements for cells which have been lost or damaged. The cells achieve functional integration and replace or compensate for the missing or damaged cells. They become a functional part of the brain rather than being merely a sophisticated method of drug administration. Genetic modification of the cells will therefore usually be restricted to the insertion of genes necessary for conditional immortalisation and cloning. Genes required for cloning may be, for example, a gene providing resistance to a selected antibiotic to enable selection. Genetic modification to enable secretion of pharmacologic agents is not preferred.

Methods for transplantation of cells into humans and animals are known to those in the art and are described in the literature in the art. The term "transplantation" used herein includes the transplantation of cells which have been grown in vitro, and may have been genetically modified, as well as the transplantation of material extracted from another organism. Cells may be transplanted by implantation by means of microsyringe infusion of a known quantity of cells in the target area where they would normally disperse around the injection site. They may also be implanted into ventricular spaces in the brain. If implanted into the neonate then they may disperse throughout the entire brain.

The phrase "intracerebral transplantation" used herein includes transplantation into any portion of the brain. Transplantation is not restricted to the front and larger part of the brain.

The following non-limiting Examples illustrate the invention.

FIGS. 1 to 20 show the results of the experiments described in Examples 3 and 5 to 8. The figures are as follows:

FIG. 1—shows the proliferation of MHP15 cells at 33° C. and 39° C. in SFM.

Figure 2:
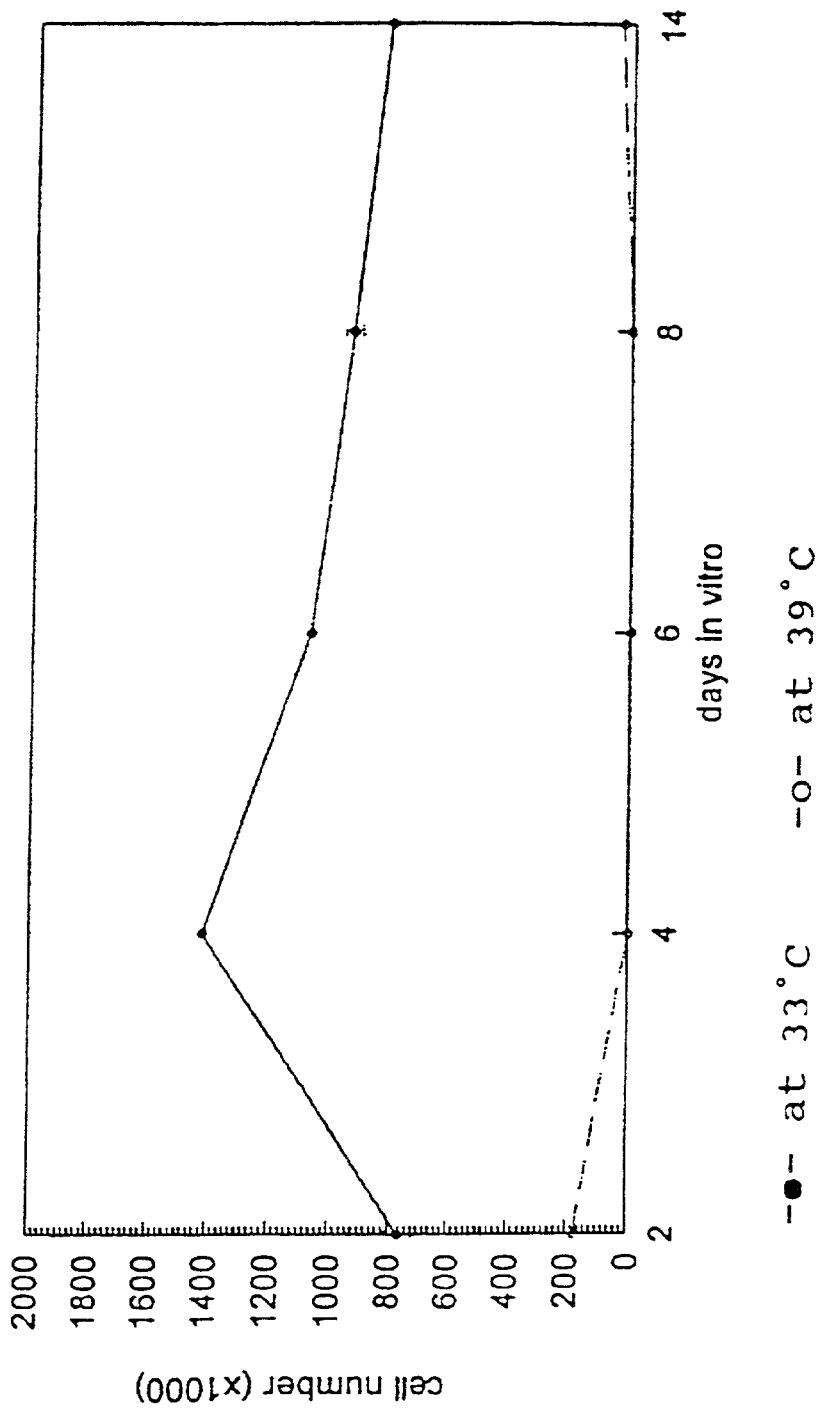

FIG. 2—shows the proliferation of MHP15 cells at 33° C. and 39° C. in SFM with gamma-interferon (12 U/ml).

Figure 3:
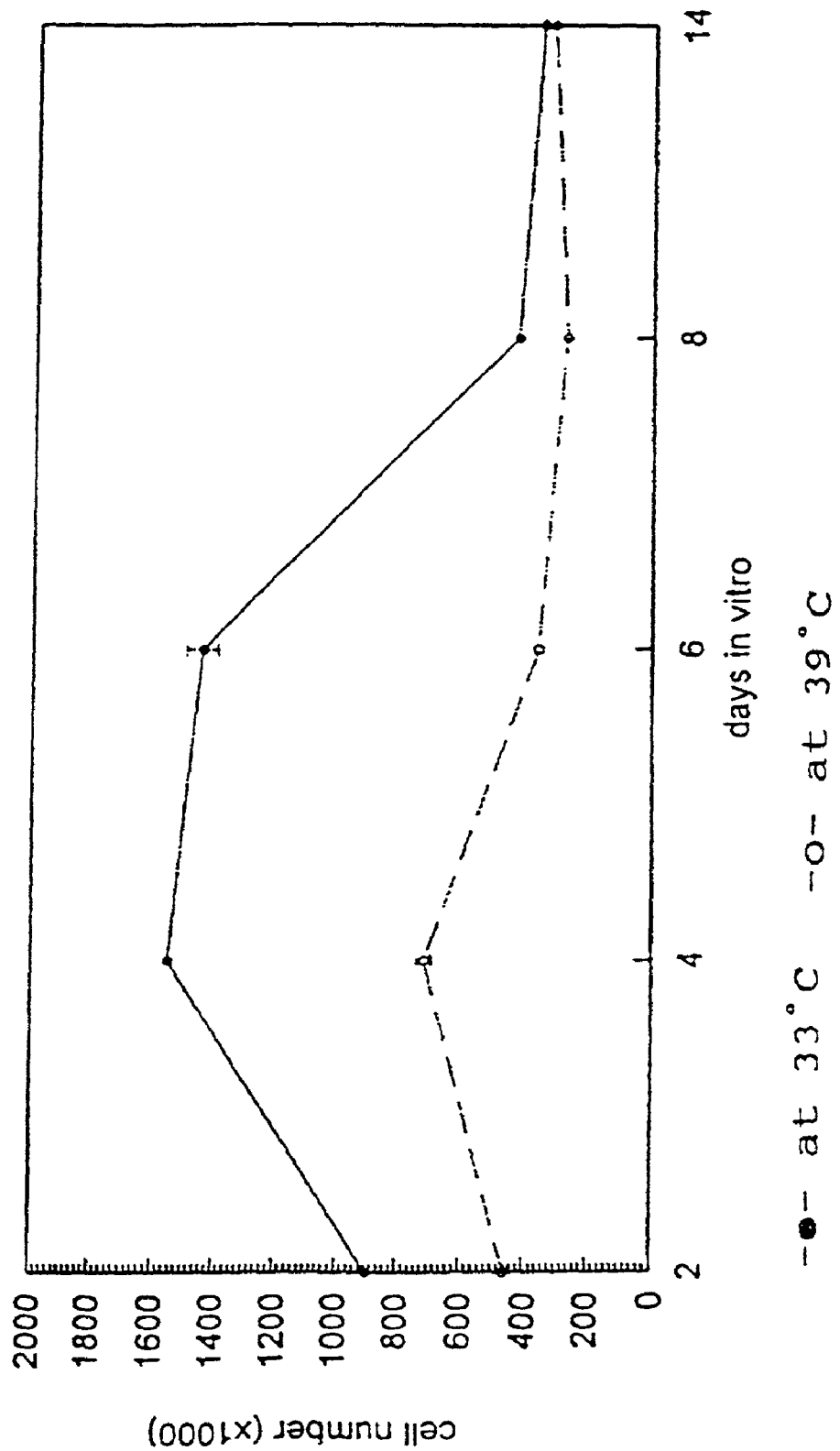

FIG. 3—shows the proliferation of MHP15 cells at 33° C. and 39° C. in SFM with FGF2 (long/ml).

Figure 4:
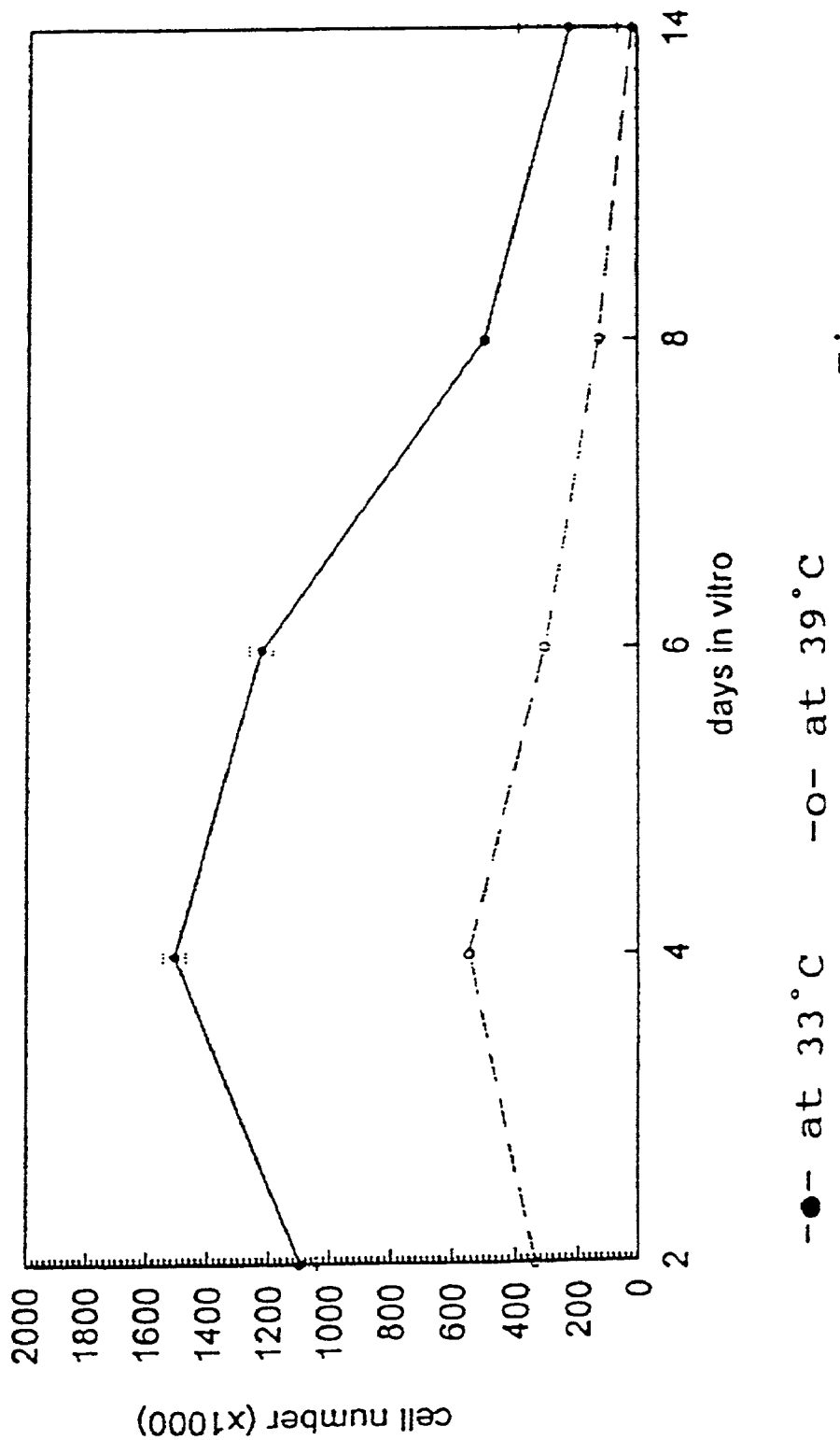

FIG. 4—shows the proliferation of MHP15 cells at 33° C. and 39° C. in SFM with gamma-interferon (12 U/ml) and FGF2 (10 ng/ml).

Figure 5:
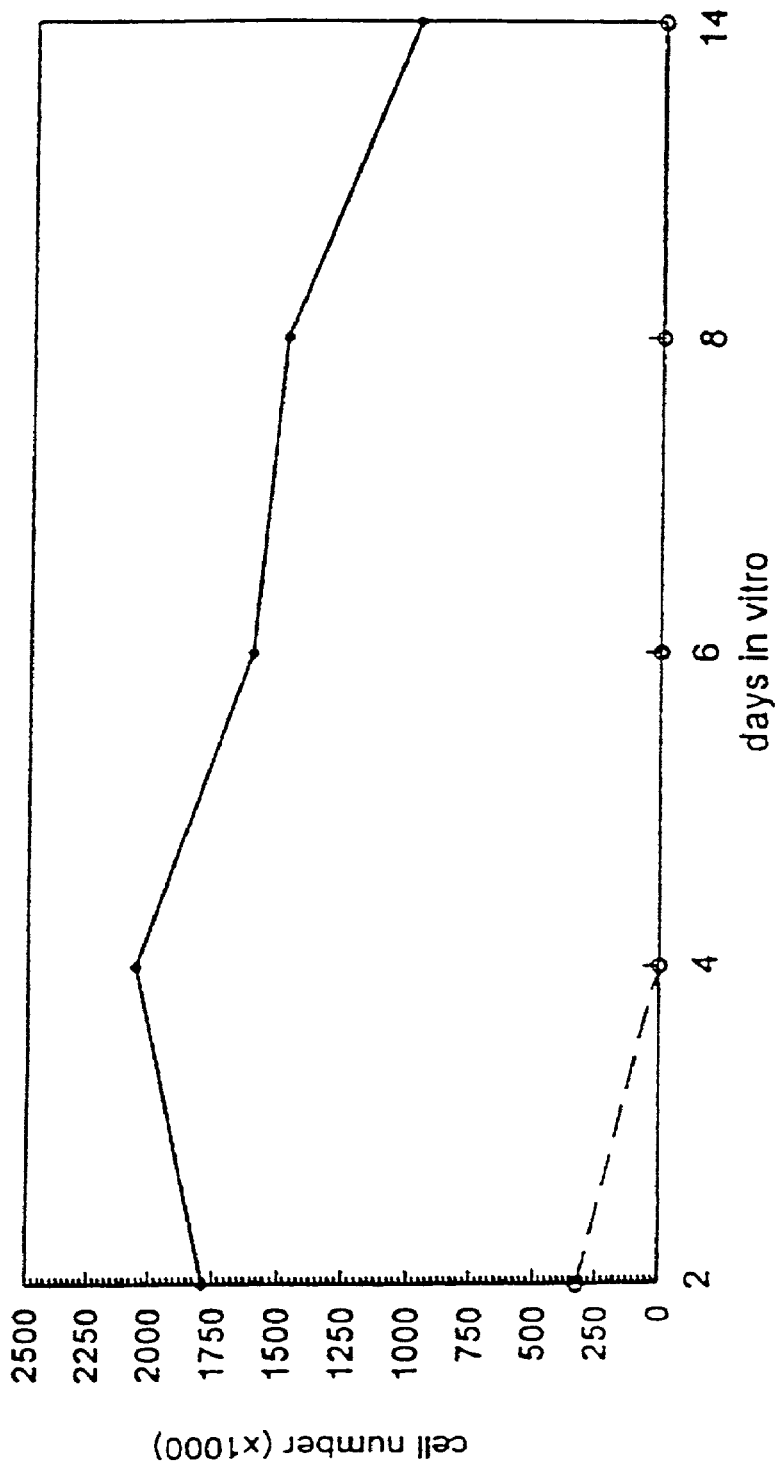

FIG. 5—shows the proliferation of MHP36 cells at 33° C. and 39° C. in SFM.

Figure 6:
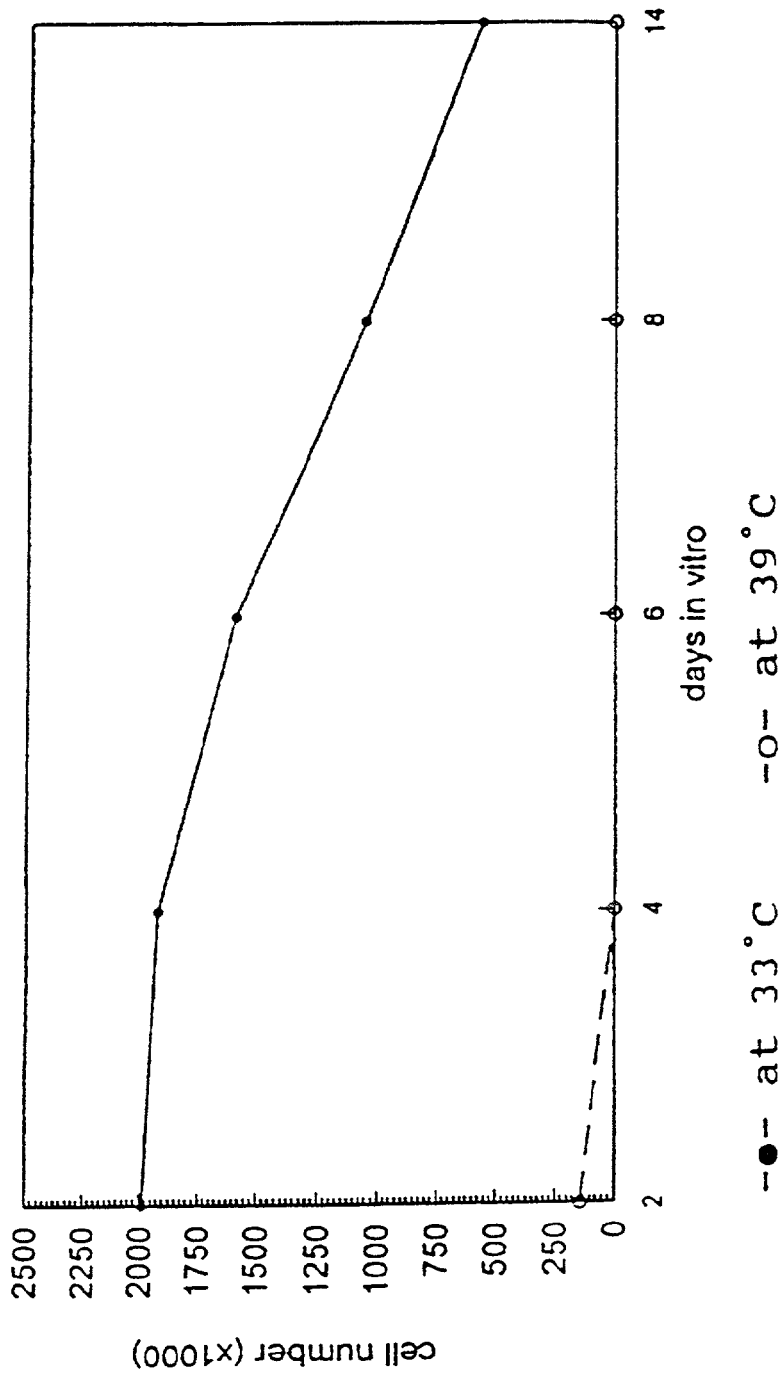

FIG. 6—shows the proliferation of MHP36 cells at 33° C. and 39° C. in SFM with gamma-interferon (12 U/ml).

Figure 7:
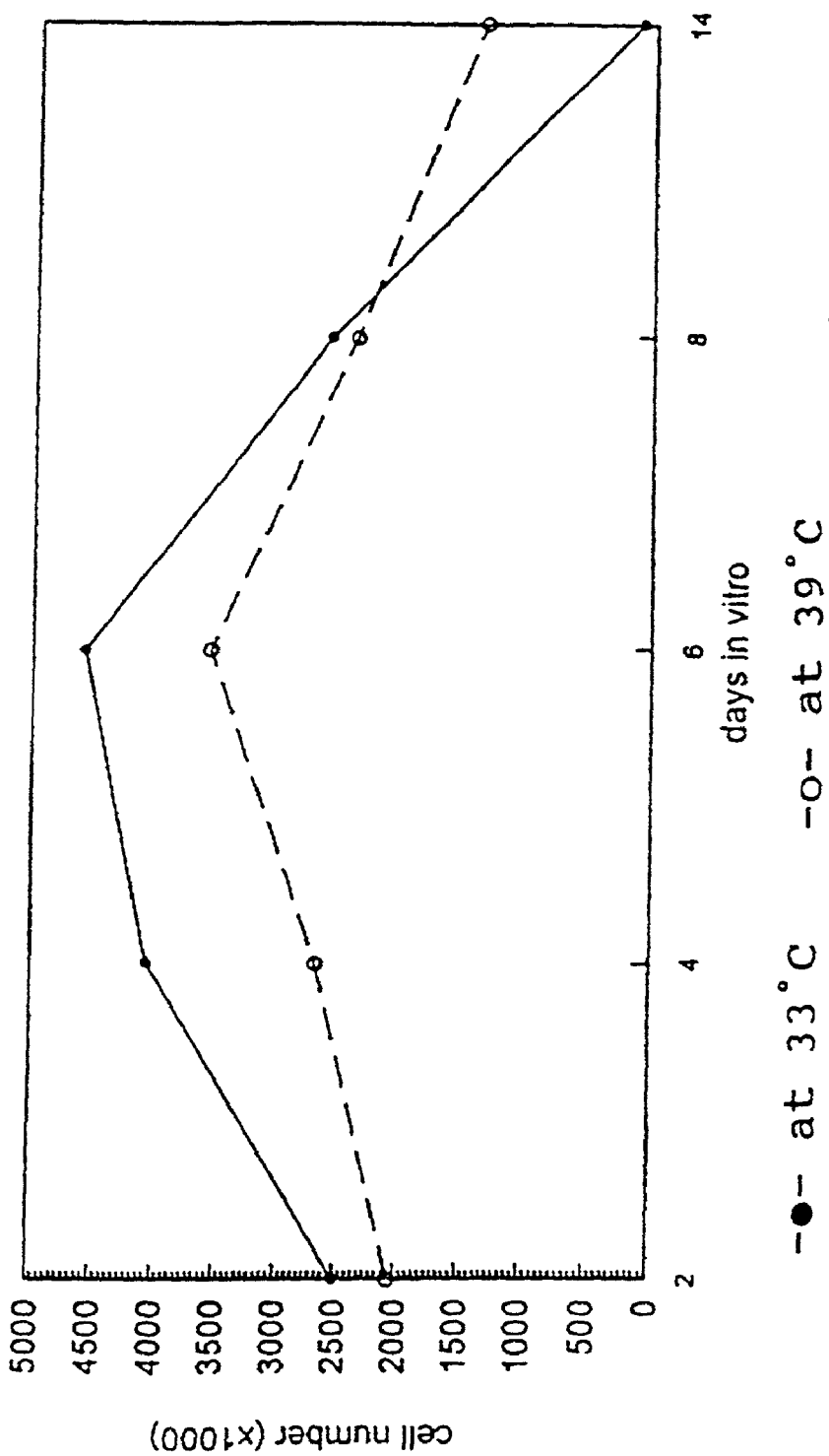

FIG. 7—shows the proliferation of MHP36 cells at 33° C. and 39° C. in SFM with FGF2 (10 ng/ml).

Figure 8:
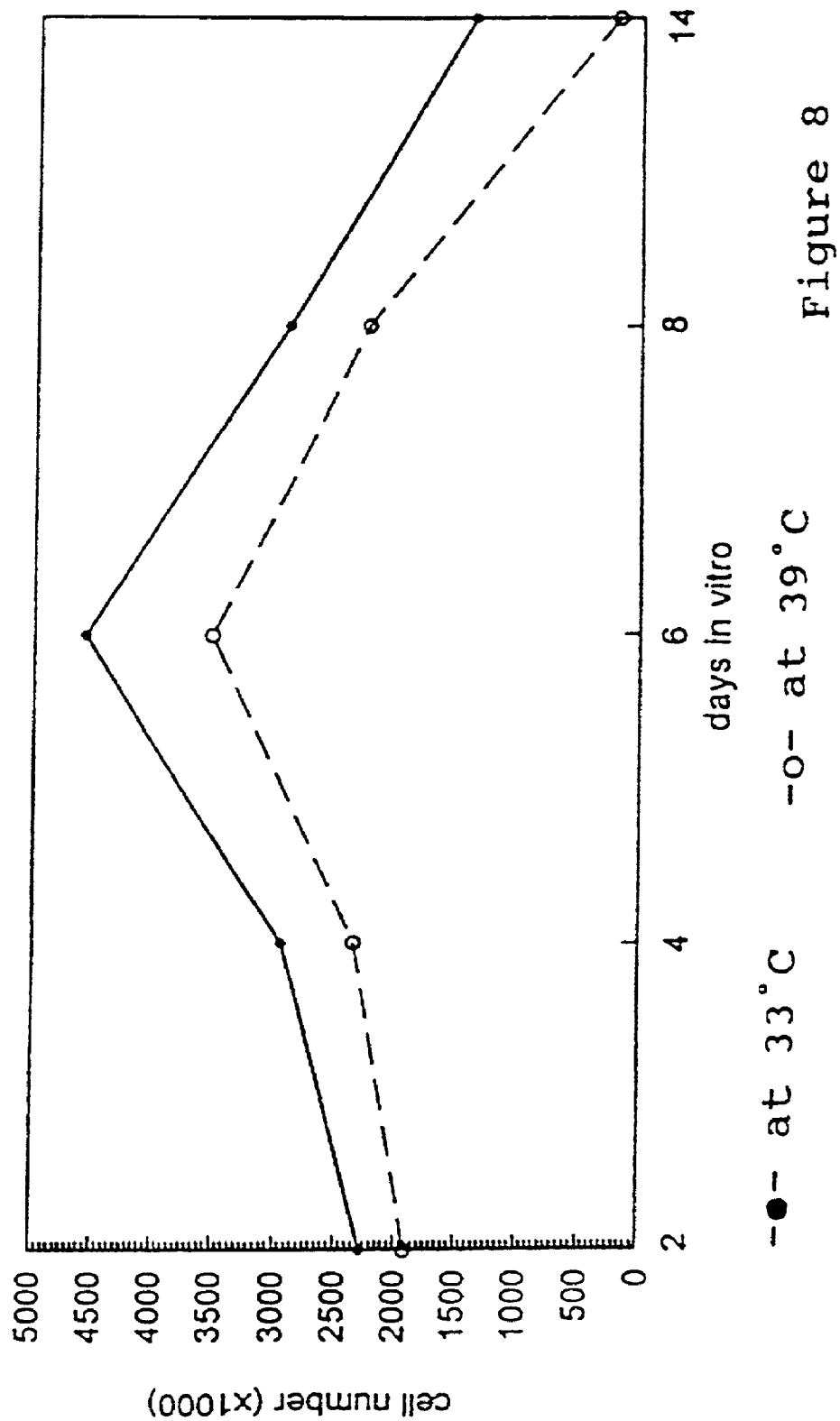

FIG. 8—shows the proliferation of MHP36 cells at 33° C. and 39° C. in SFM with gamma-interferon (12 U/ml) and FGF2 (10 ng/ml).

Figure 9:
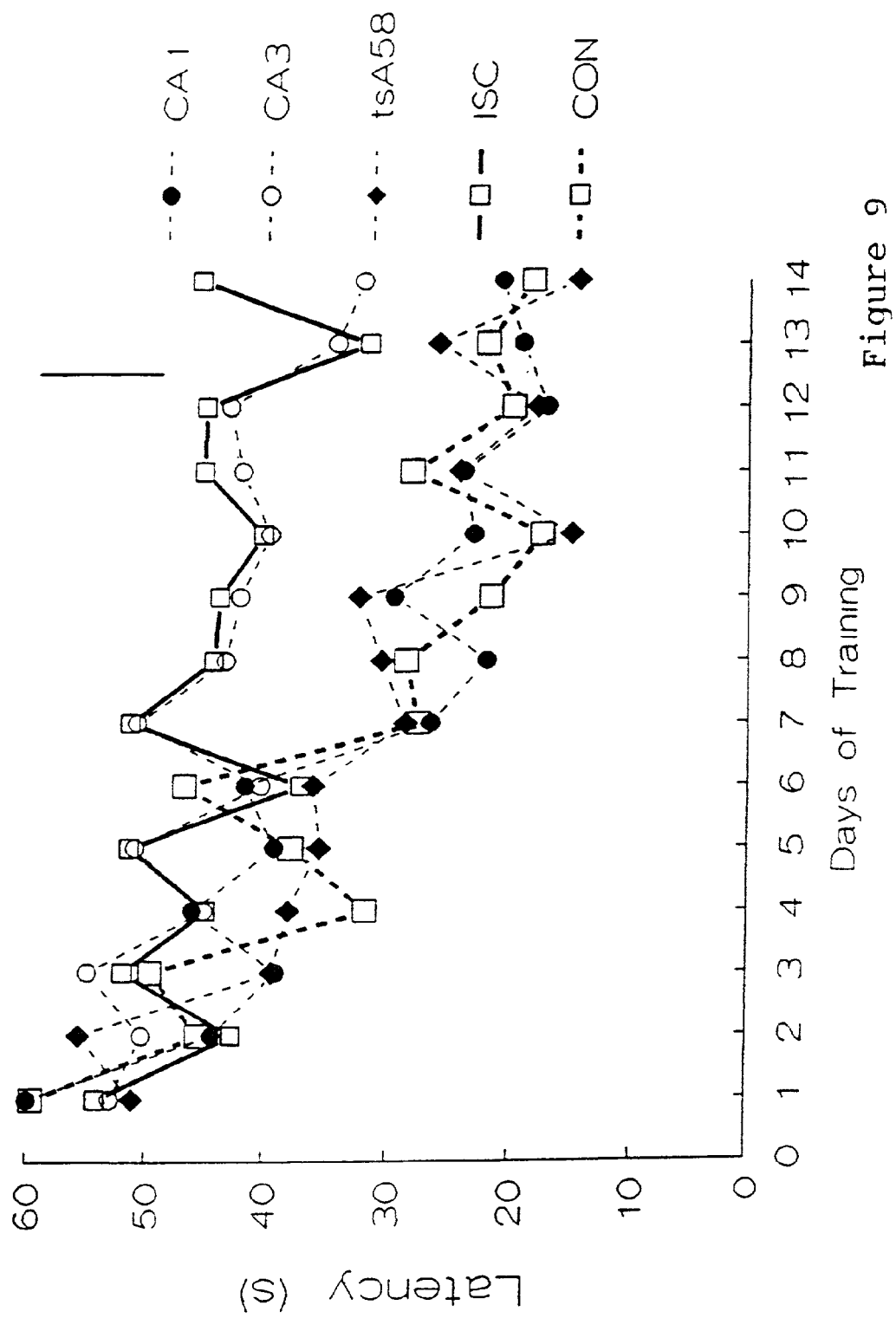

FIG. 9—shows the latency of rats in a Morris water maze over time for sham-lesioned control rats which received sham grafts (CON), ischaemic rats which received sham grafts (ISC), ischaemic rats which received an implant of CA1 cells (CA1), CA3 cells (CA3), or of a mixed population of conditionally immortal hippocampus precursor cells taken from a H-2K$^b$-tsA58 transgenic mouse (tsA58).

Figure 10:
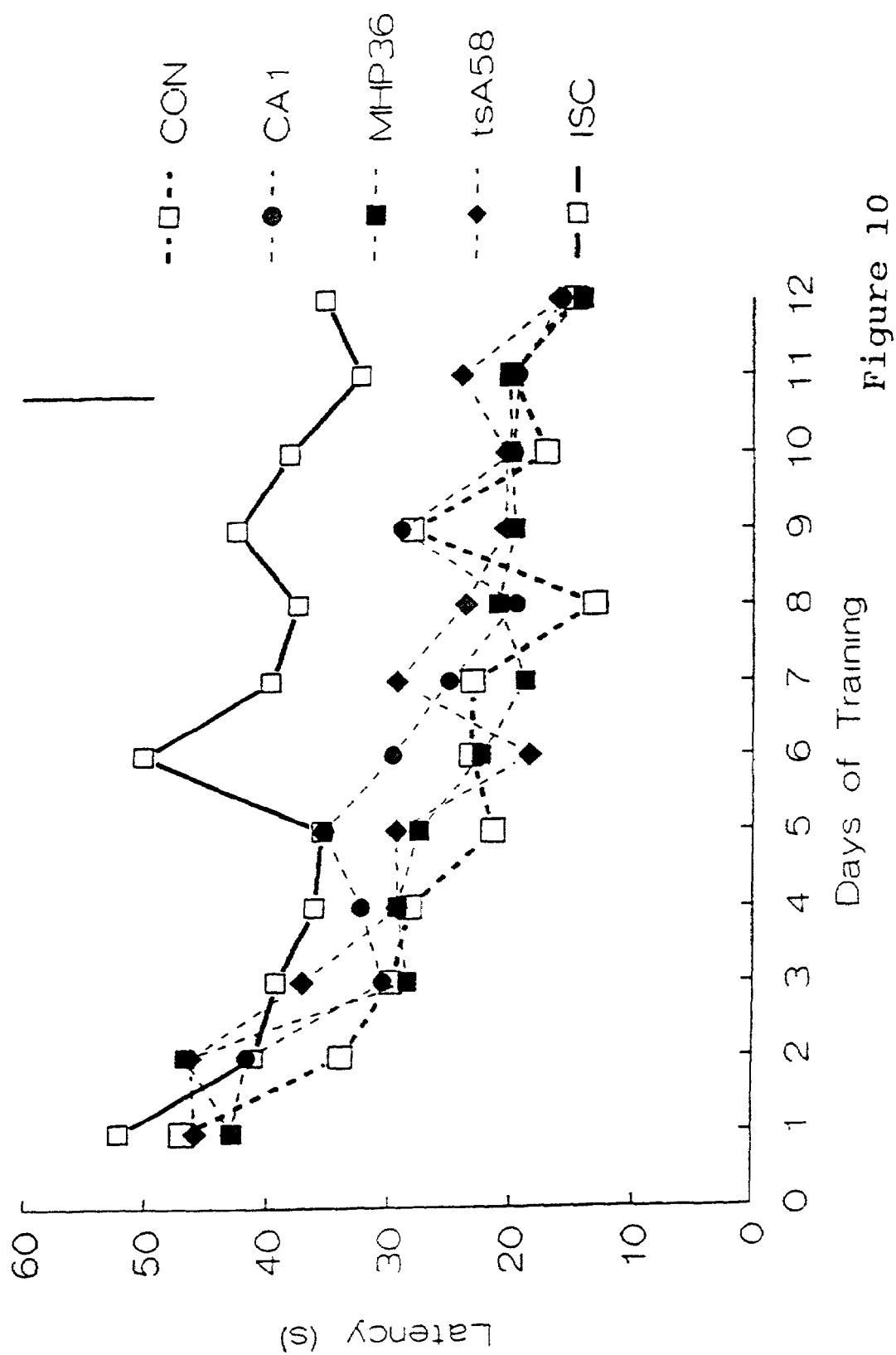

FIG. 10—shows the latency of rats in a Morris water maze over time for sham-lesioned control rats which received sham grafts (CON), ischaemic rats which received sham grafts, (ISC), ischaemic rats which received an implant of CA1 cells (CA1), of cells of the MHP36 cell line (MHP36) or of a mixed population of conditionally immortal hippocampus precursor cells taken from a H-2K$^b$-tsA58 transgenic mouse (tsA58).

Figure 11:
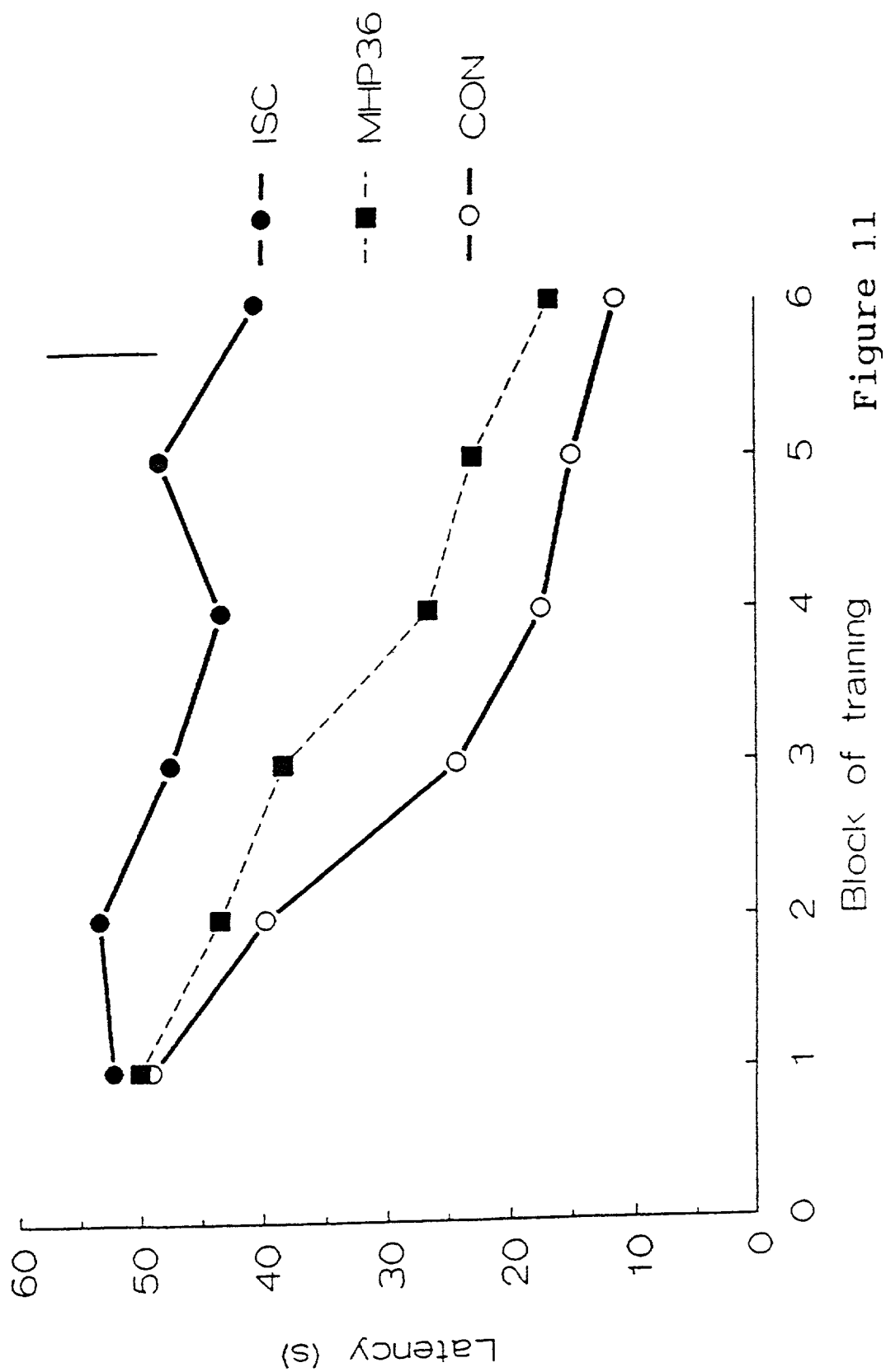

FIG. 11—shows the latency of rats in a Morris water maze over time for sham-lesioned control rats which received sham grafts (CON), ischaemic rats which received sham grafts (ISC) and ischaemic rats which received an implant of cells of the MHP36 cell line (passage 24 to 32) (MHP36).

Figure 12:
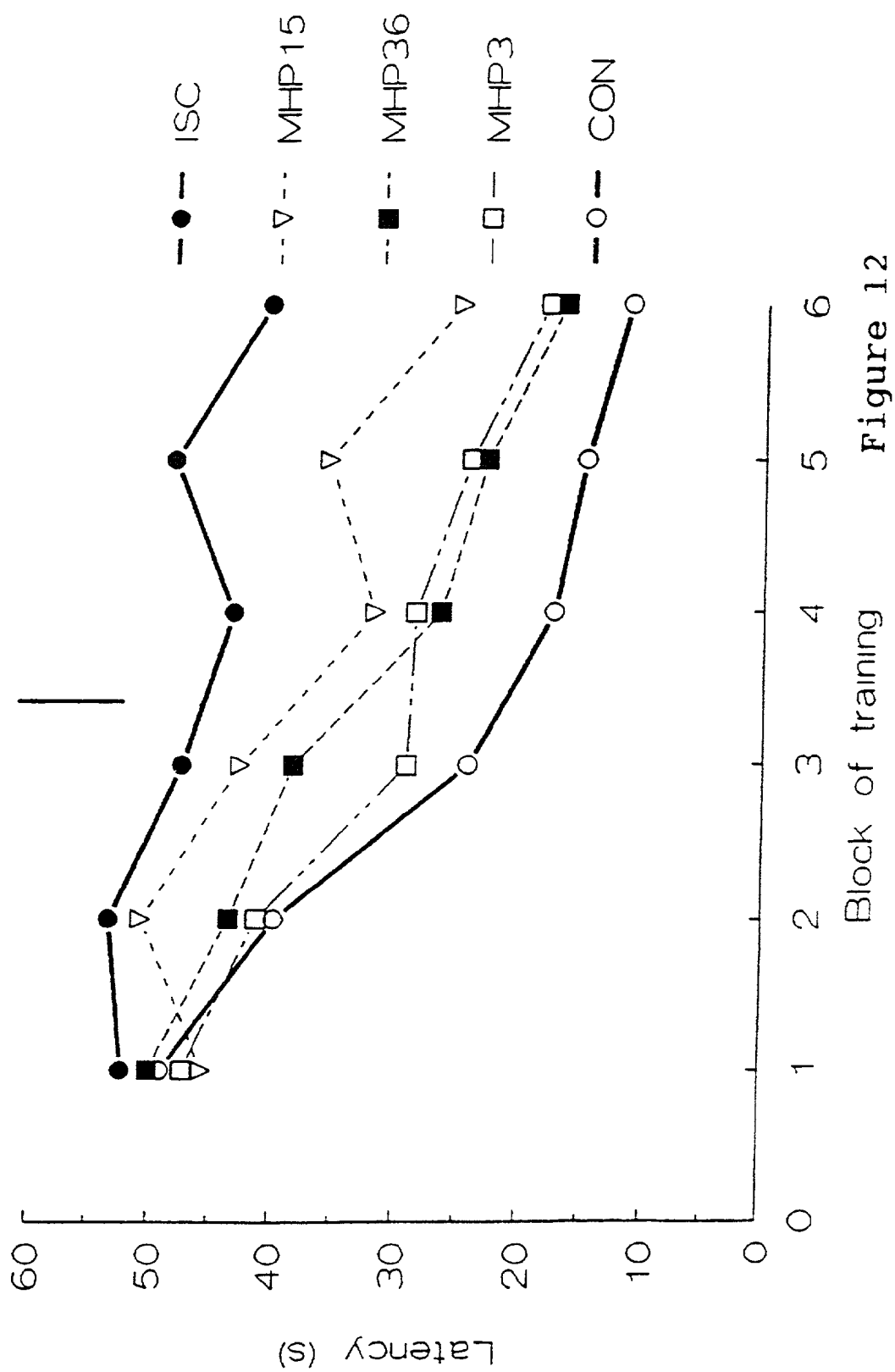

FIG. 12—shows the latency of rats in a Morris water maze over time for sham-lesioned control rats which received sham grafts (CON), ischaemic rats which received sham grafts (ISC), ischaemic rats which received an implant of cells of the MHP36 cell line (MHP36), of cells of the MHP15 cell line (MHP15) or of cells of the MHP3 cell line (MHP3).

Figure 13:
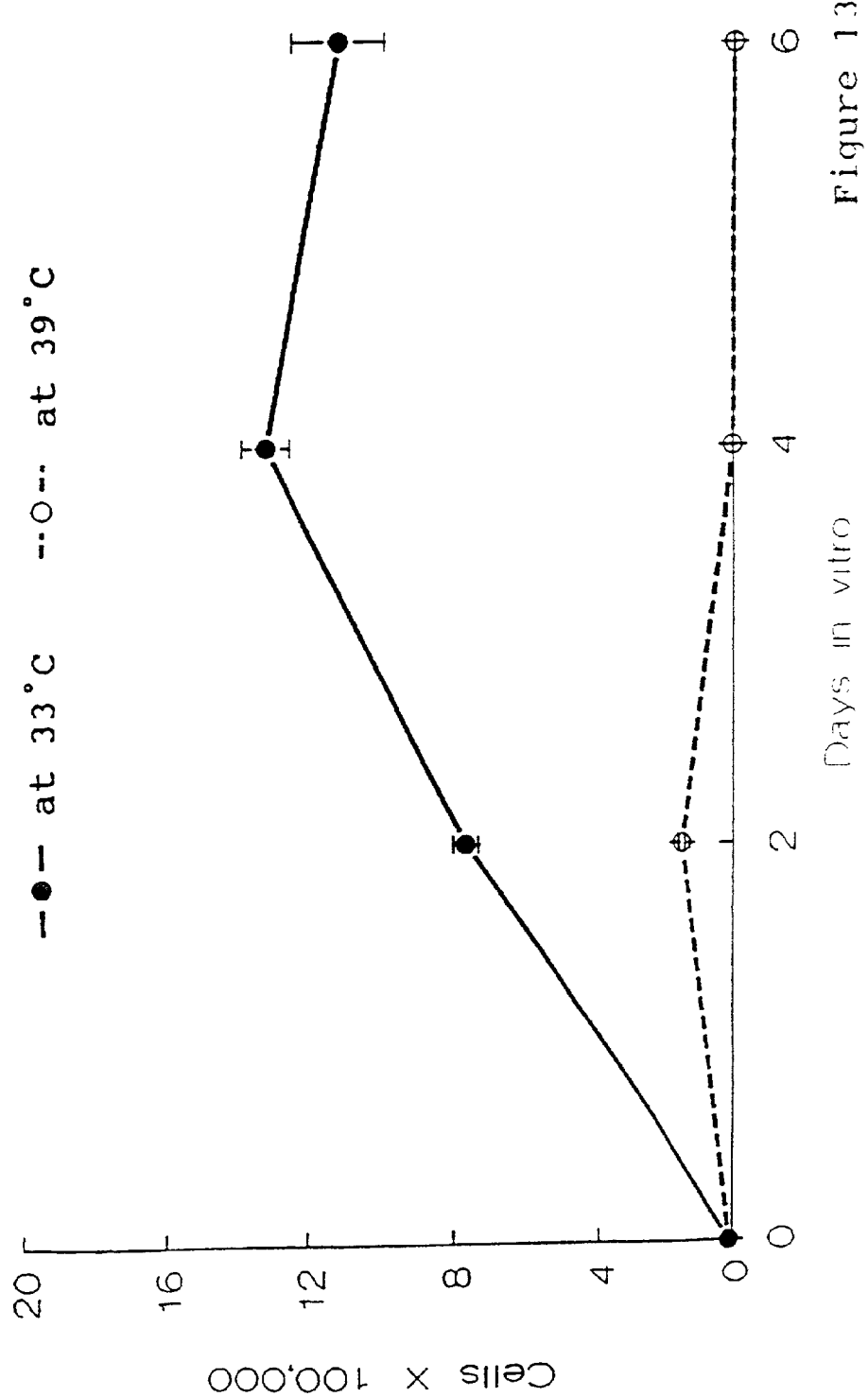

FIG. 13—shows the proliferation of MHP15 cells at 33° C. and 39° C. in SFM, as in FIG. 1 but for days 0 to 6.

Figure 14:
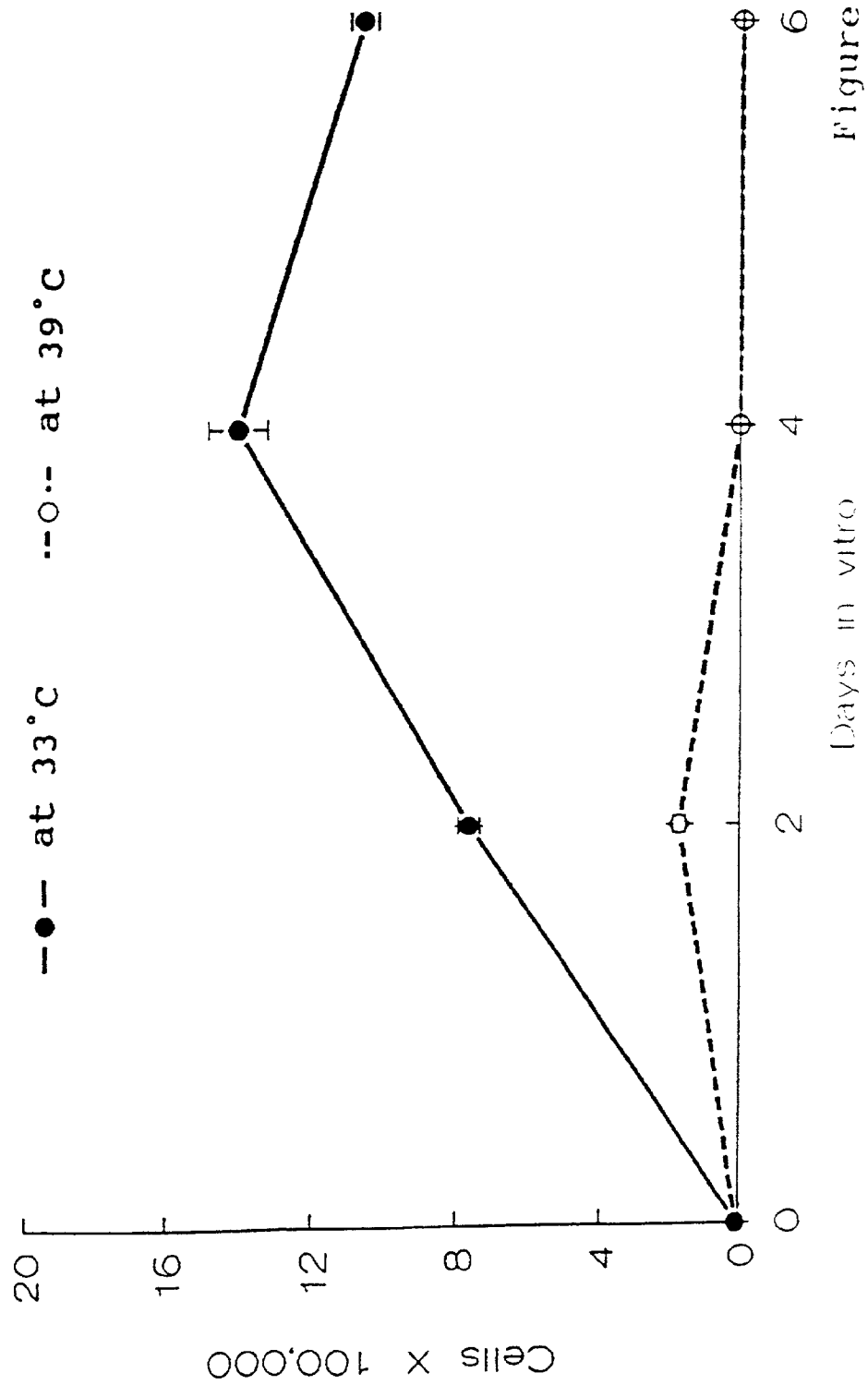

FIG. 14—shows the proliferation of MHP15 cells at 33° C. and 39° C. in SFM with gamma-interferon (12 U/ml), as in FIG. 2 but for days 0 to 6.

Figure 15:
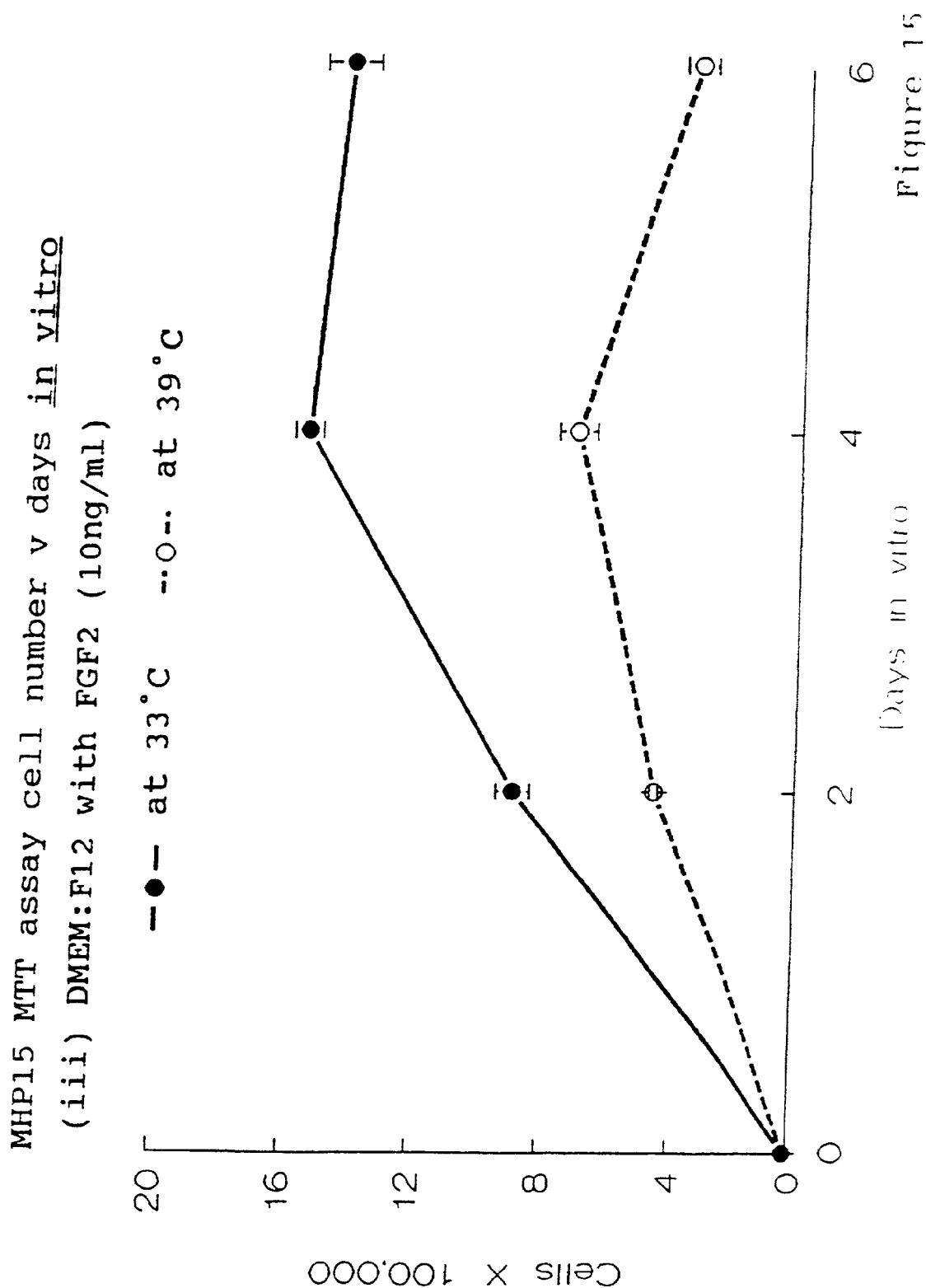

FIG. 15—shows the proliferation of MHP15 cells at 33° C. and 39° C. in SFM with FGF2 (10 ng/ml), as in FIG. 3 but for days 0 to 6.

Figure 16:
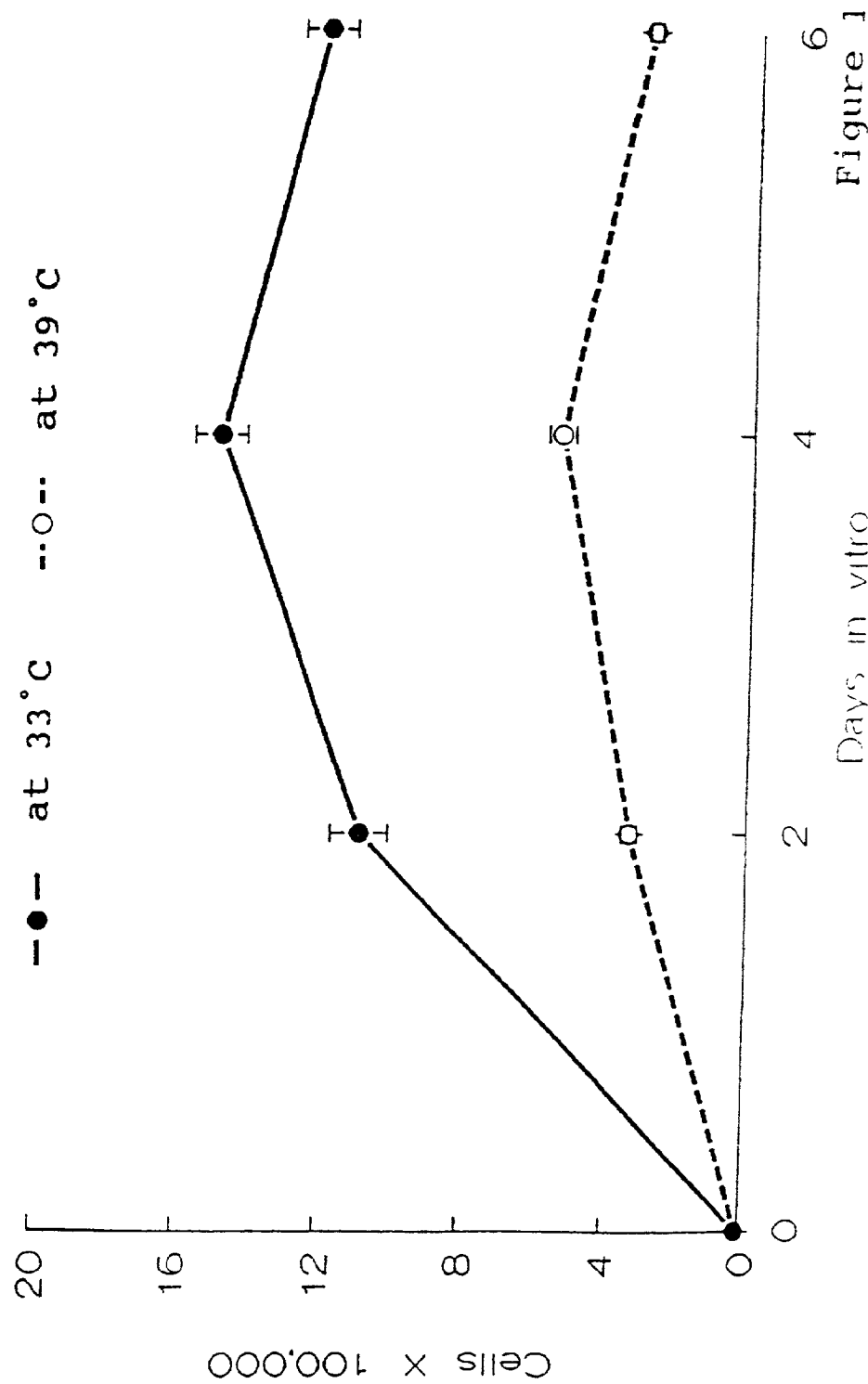

FIG. 16—shows the proliferation of MHP15 cells at 33° C. and 39° C. in SFM with gamma-interferon (12 U/ml) and FGF2 (10 ng/ml), as in FIG. 4 but for days 0 to 6.

Figure 17:
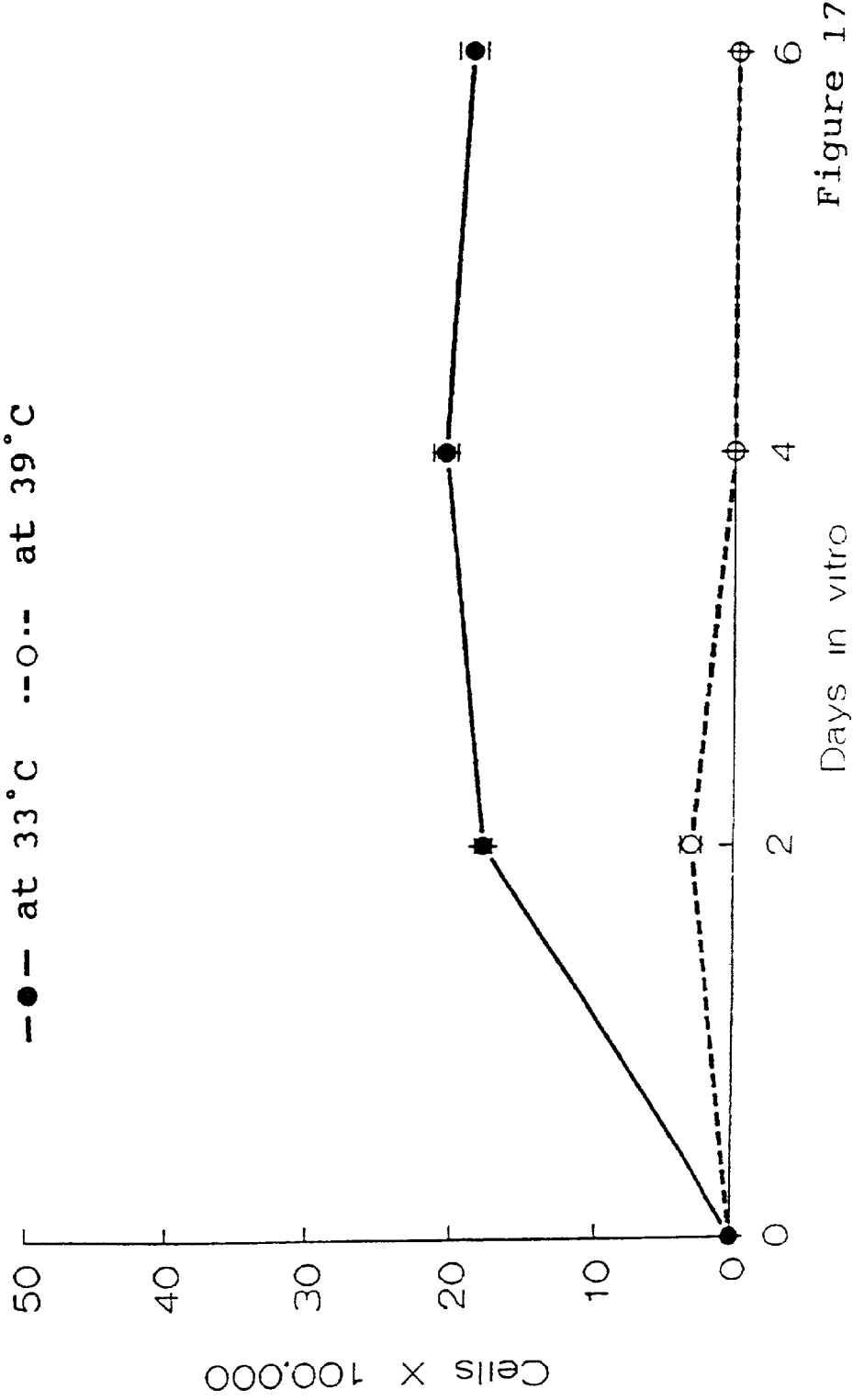

FIG. 17—shows the proliferation of MHP36 cells at 33° C. and 39° C. in SFM, as in FIG. 5 but for days 0 to 6.

Figure 18:
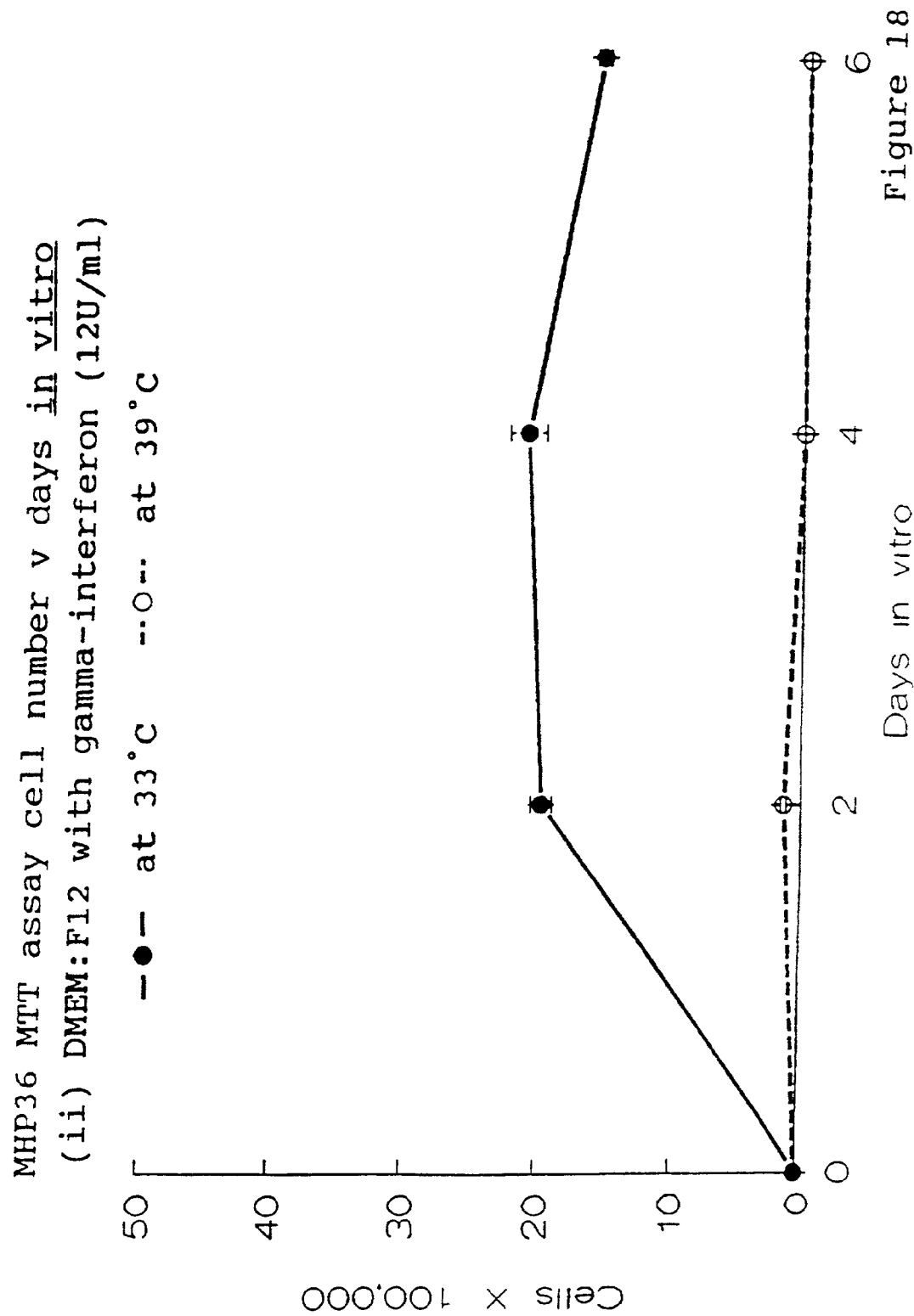

FIG. 18—shows the proliferation of MHP36 cells at 33° C. and 39° C. in SFM with gamma-interferon (12 U/ml), as in FIG. 6 but for days 0 to 6.

Figure 19:
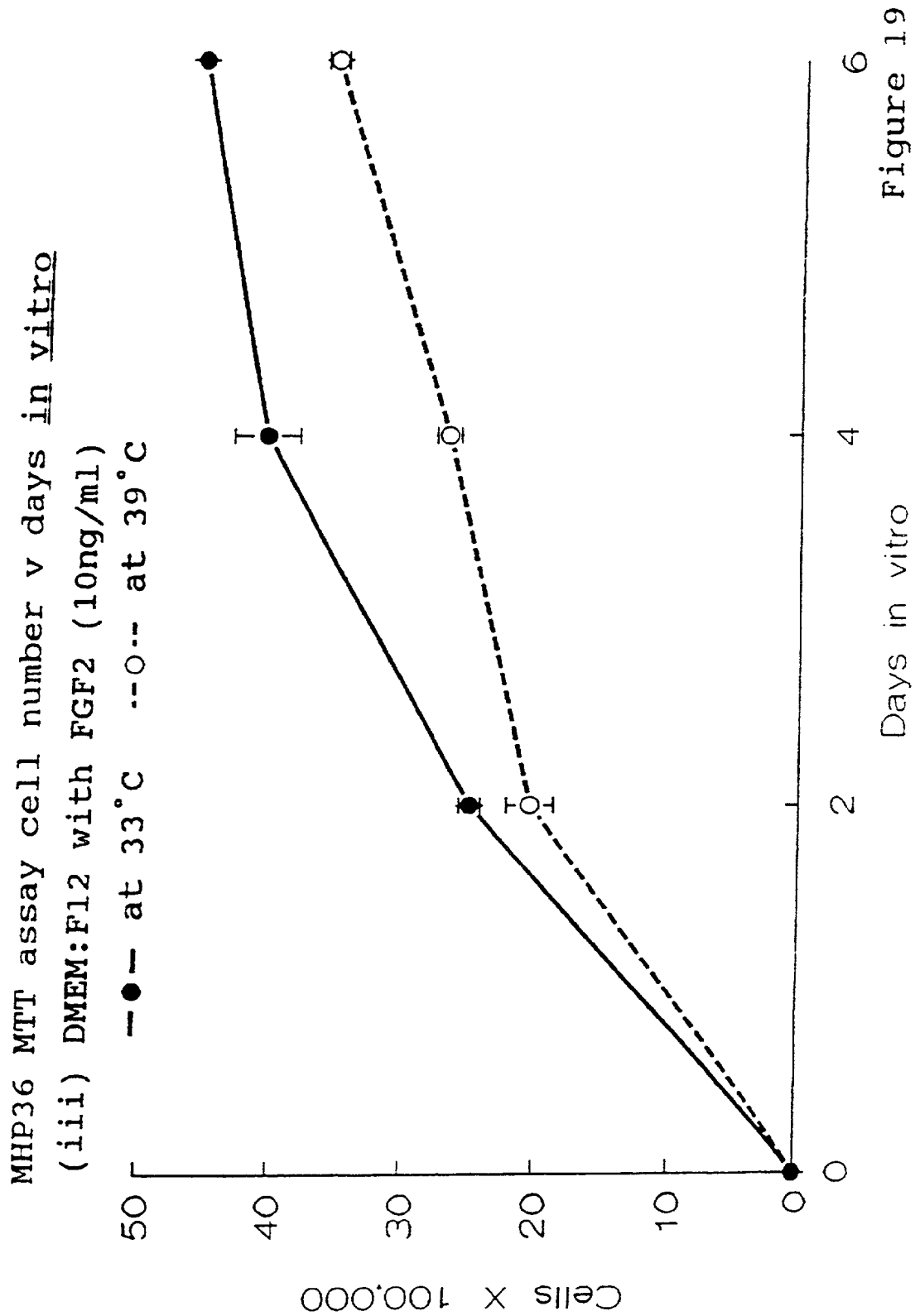

FIG. 19—shows the proliferation of MHP36 cells at 33° C. and 39° C. in SFM with FGF2 (10 ng/ml), as in FIG. 7 but for days 0 to 6.

Figure 20:
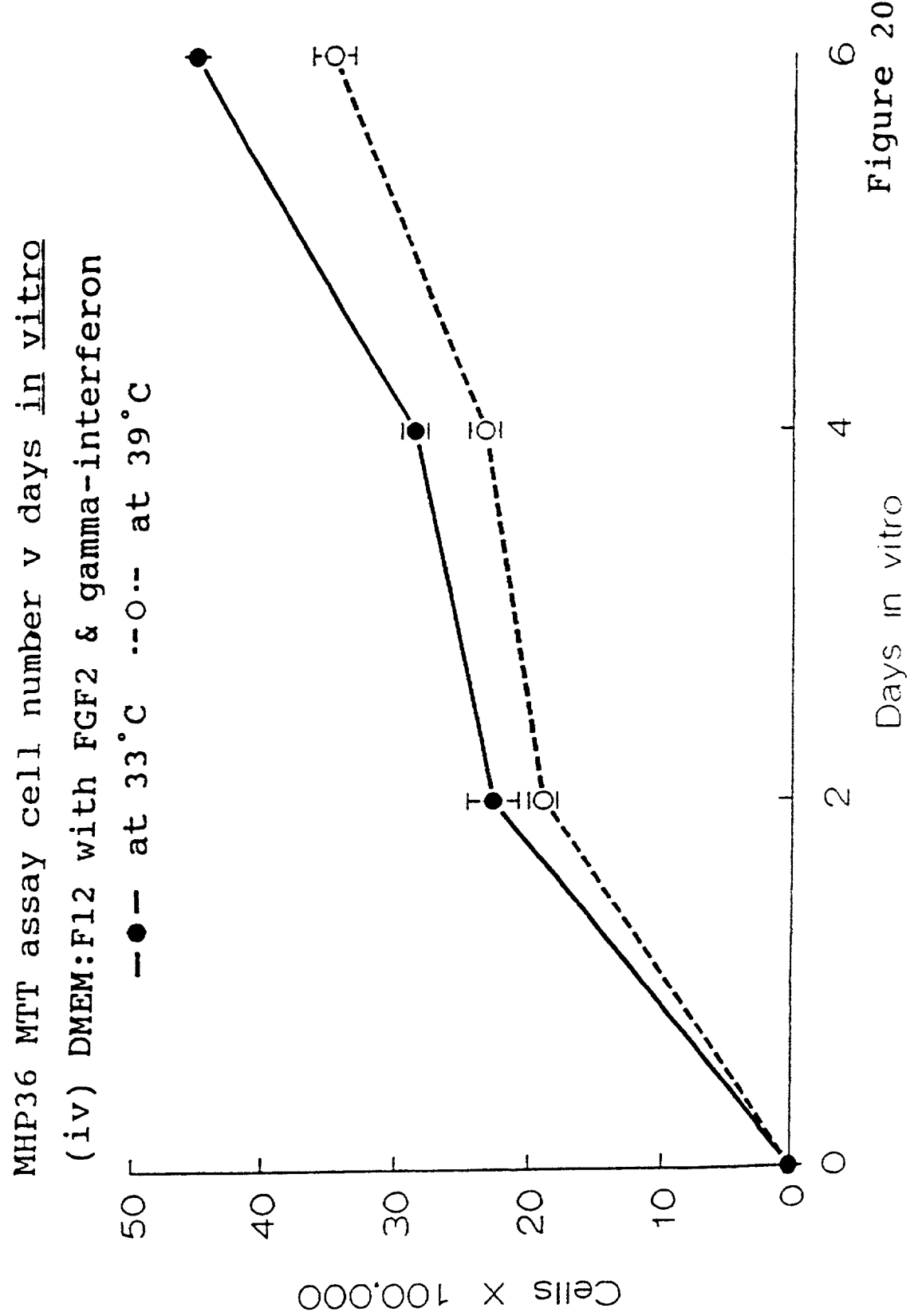

FIG. 20—shows the proliferation of MHP36 cells at 33° C. and 39° C. in SFM with gamma-interferon (12 U/ml) and FGF2 (10 ng/ml), as in FIG. 8 but for days 0 to 6.

EXAMPLE 1

Preparation of Mixed Population Cultures

Hippocampi were dissected from E14 H-2K$^b$-tsA58 mice. A cell suspension was prepared after both trypsinisation and mechanical dissociation and cells were plated at a concentration of $45 \times 10^3$ to $50 \times 10^3$ cells/ml into 10 cm$^2$ culture dishes. The cells were cultured in DMEM: F12 serum-free medium (SFM) with the following additions: bovine serum albumen (0.0286%); transferrin (0.1 mg.ml); putrescine (16.2 µg/ml); insulin (5 µg/ml); progesterone (0.062 µg/ml); selenium (0.0383 µg/ml); L-glutamine (2 mM); L-thyroxine (0.4 µg/ml); tri-iodothyronine (0.337 µg/ml); heparin (1OUSP units/ml); penicillin/streptomycin (10,000:1000 units/ml) all obtained from Sigma. In addition basic fibroblast growth factor, previously known as bFGF and now known as FGF2, (FGF2-10 ng/ml) and gamma-interferon (g-IFN-12 U/ml) were added to the cells and they were incubated at 33° C. in 5% CO$_2$. Every 2 to 3 days half the medium was replaced and all the FGF2 and g-IFN.

EXAMPLE 2

Production of Clonal Lines pPGKB-geo plasmid (obtained from P. Soriano) which consisted of a lacZ and neomycin resistance fusion driven by a pGK promoter was grown overnight at 37° C. in Luria Bertani broth and then purified using a commercially available kit (Qiagen, Germany). The purified plasmid DNA was linearised using the restriction enzyme Sal 1 (Promega, U.K.) then sterilised and resuspended in the TE buffer at a final concentration of 1 mg/ml. A mixed population of hippocampal neuroepithelial cells as prepared in Example 1 were electroporated in order for the cells to incorporate the lacZ fusion gene.

Cells were seeded at a concentration of $10^5$ to $10^6$ cells/plate in SFM (with the additions listed in Example 1) with the appropriate FGF2 and g-IFN additions and after 24 hours the medium was replaced with SFM containing G418 (a neomycin-like antibiotic) (200 µg/ml) which would allow only those cells which had incorporated the plasmid correctly to be able to express G418 resistance. Medium was replaced 2 to 3 times a week and the cells were left for 4 to 6 weeks to allow clones to develop.

Clones that were selected were discrete from one another and picked using glass cloning rings which had been dipped in silicon grease. The clonal cells were transferred to 24 well plates after a brief incubation of 5 mins with EDTA/EGTA (1:100) solution at 37° C. After several days these cells became confluent and were transferred into 6 well plates and then into 10 cm$^2$ culture dishes, thereafter being treated exactly the same as the mixed population non-transfected lines, as described above, with the exception of the G418 additions. Of the 32 clones picked, 9 clones were expanded into permanent cell lines.

All of these clonal hippocampal lines were shown to be conditionally immortal; cell counts by chromogenic MTT assay showed $1-2 \times 10^3$-fold proliferation from original plating densities in permissive conditions in serum-free media without added FGF2 at 2 to 6 days in vitro (hereinafter referred to as "DIV") with a rapid reduction in plated cell numbers at nonpermissive conditions (39° C., gamma-IFN). The hippocampal neuroepithelial population from which these lines were derived, however, required supplementation with FGF2 for proliferation. Two of the nine lines were, in addition, FGF2-responsive, substantially increasing their proliferation rate in both permissive and nonpermissive culture in the presence of this growth factor.

Lines have been maintained for multiple passages and frozen stocks have been thawed and cultured without change of phenotype.

EXAMPLE 3

Proliferation of Clonal Lines MHP15 and MHP36 in Vitro (Cell lines MHP36 and MHP15 were previously known as C36 and C15 respectively. The C36 and C15 references were used in the application from which this current application claims priority. The cell lines are the same cell lines, only the names have changed.)

Cells from two of the permanent cell lines were plated at a density of $8-12 \times 10^3$ cells/well into 96 well plates in serum free DMEM:F12 medium (SFM) with the addition of basic fibroblast growth factor (FGF2-10 ng/ml) and g-interferon (12 U/ml) for 24 hours at 33° C. with 5% CO$_2$. Following this period all of the medium, FGF2 and g-interferon was removed and each column consisting of 8 wells was treated with either:

(i) SFM with no supplements;
(ii) SFM with g-interferon (12 U/ml);
(iii) SFM with FGF2 (10 ng/ml); or
(iv) SFM with both g-interferon (12 U/ml) and FGF2 (10 ng/ml);

for 2, 4, 6, 8, and 14 days in vitro at either 33° C. or 39° C. Cells were counted at each time point under each temperature and supplement condition using a chromogenic MTT assay. Both cell lines show clear temperature sensitivity in SFM both with and without g-interferon; cells rapidly proliferate up to 200 fold plating density at the permissive temperature (33° C.), but show minimal proliferation at the non-permissive temperature (39° C.). The addition of FGF2 enhances proliferation at both temperatures in the MHP36 line; but has only a slight effect on the MHP15 line; indicating the cell lines differ in their responsiveness to this growth factor.

FIGS. 1 to 4 show the results for the MHP15 cell line for up to 14 days and FIGS. 13 to 16 show the results in greater detail for days 0 to 6. FIGS. 5 to 8 show the results for the MHP36 cell line for up to 14 days and FIGS. 17 to 20 show the results in greater detail for days 0 to 6.

EXAMPLE 4

MHP15 AND MHP36 Clonal Cell Lines Have Neuronal and Glial Potential when Differentiated in Vitro Cells were prepared for immunocytochemistry using a range of markers under both permissive conditions (33° C. plus g-interferon with added FGF2) and nonpermissive conditions (39° C.) in SFM with the addition of the differentiating agent dibutyryl CAMP (1 mM). $50-100 \times 10^3$ cells from each line were plated on fibronectin treated chamber slides in SFM with FGF2 and g-interferon at 33° C. for 48 hours. Half the slides were fixed at this stage and the other half had media removed and substituted with SFM containing 1 mM dibutyryl cAMP and maintained at 39° C. These slides were fixed after 2 to 8 days in vitro with 4% paraformaldehyde. The Table shows the proportion of all cells in 5 randomly selected fields expressing the marker for progenitor cells, Nestin; the neuronal marker, neurone specific enolase (NSE); the glial marker, glial fibrillary acidic protein (GFAP) and the marker for the immortalising gene antigen, SV40. Both cell lines show neuronal and glial phenotypes after, but not before, differentiation.

| DAYS IN VITRO-TEMPERATURE | NESTIN % cells labelled | NSE % cells labelled | GFAP % cells labelled | SV40 % cells labelled |
|---|---|---|---|---|
| MHP15 CLONAL LINE | | | | |
| 2–33° C. | 100 ± 0 | 0 ± 0 | 0 ± 0 | 100 ± 0 |
| 2–39° C. | 100 ± 0 | 12.4 ± 2.2 | 3.8 ± 1 | 100 ± 0* |
| MHP36 CLONAL LINE | | | | |
| 2–33° C. | 100 ± 0 | 0 ± 0 | 0 ± 0 | 100 ± 0 |
| 2–39° C. | 100 ± 0 | 59.3 ± 7.0 | 12.2 ± 3.3 | 38.6 ± 16.1 |

*SV40 is down-regulated after 4 days in vitro in the MHP15 line.

Further Characterisation of MHP36 Clonal Line

The MHP36 cell line was further characterised at 2 DIV in both permissive and nonpermissive culture. It was found that the cells were >95% X-gal labelled (i.e. showed a histochemical reaction to the β-gal transduce marker) in permissive conditions. The cells were also tested with two further antibodies, one for the neuronal marker PGP 9.5 (Wilson et. al., 1988) and one for bromodeoxyuridine (BrdU) after one hour incubation with BrdU labelling medium as a marker for dividing cells. In permissive culture BrdU stained cells were found throughout the culture. There were no PGP 9.5 cells in permissive culture.

Following a switch to nonpermissive conditions in serum-free media (SFM) without additions, this cell line stopped dividing and the majority of cells died without differentiating into mature neuronal or glial phenotypes. However, in the presence of forskolin or retinoic acid (both of which are differentiating agents) the cultures could be maintained for longer periods (5–14 DIV) and a proportion of the cells showed neuronal or glial phenotypes by 2 DIV. The MHP36 cells showed a flat-cell morphology in the presence of retinoic acid ($10^{-9}$M) with a number of GFAP-positive fibrillary cells, SV40 expression was reduced to 30% and BrdU staining to 5% of cells; no PGP 9.5 stained cells were found. In the presence of forskolin ($10^{-8}$M), however, bipolar PGP 9.5-positive cells were frequently found, many cells having long neuritic processes. GFAP-stained fibrils were not found in the cultures, SV40 expression was down-regulated (to 42% of total cells) and BrdU staining was found in 4% of the culture. These findings further confirm that MHP36 is a pluripotent neural precursor cell line whose lineage fate is at least partly determined by inductive signalling.

EXAMPLE 5

Grafted H-2K$^b$-tsA58 hippocampal precursor cells, like cell suspensions of CA1 cells, restore spatial learning and memory in rats with ischaemic lesions of CA1.

The effects of grafts of cell suspensions of E19 CA1 (CA1), E19 CA3 (CA3) and expanded cultures of E14 transgenic H-2K$^b$-tsA58 hippocampal neuroepithelial cells (tsA58) (harvested at Passage 5) on acquisition of a hidden platform position in the Morris water maze following 15 minutes of 4VO ischaemia (ISC), producing selective lesions to CA1 were studied. The methods described in the paper by Sinden et al, 1995, especially those described in section 9 of the paper, were followed except where indicated to the contrary. The paper gives details of the method used to cause ischaemia, of methods of transplantation and of using the Morris water maze test. A brief summary of the procedure is given below.

Transient global ischemia was induced in male Wistar rats by the 4VO method in which the vertebral arteries were electrocoagulated through the alar formanae on the first cervical vertebrae, under 2% halothane anaesthesia (in 70% nitrous oxide and 30% oxygen), and silastic ties were inserted around the carotids and brought to the surface. Twenty four hours later the ties were tightened and clamped for 15 minutes. Rats that failed to lose righting reflex within two minutes were not included in the experiments. Wounds were rapidly sealed with clips and lignocaine applied.

H-2K$^b$-tsA58 cells were removed from permissive culture and resuspended in Hank's balanced salt solution with 1 mM n-acetyl-L-cysteine ready for grafting. The cells were pulsed with 0.5 μCi/ml $^3$H-Thymidine 48 hours before removal.

Grafts were bilaterally targeted to the dorsal CA1 cell field (2 sites/hemisphere, 2 μl/site, 25K cells/μl for each cell-type graft) and rats were grafted 2 to 3 weeks after ischaemia surgery. The rats with grafts of tsA58 cells were treated every other day for 14 days post-transplantation with the immunosuppressant, cyclosporin A (Sandoz, 2.5 mg/rat in Cremophore EL, i.m.). Training (2 trials/day) began 12 weeks post-transplantation (Number of subjects (Ns)=7 to 11/group).

Sham-lesioned control rats underwent cauterisation of the vertebral arteries but no ligation of the carotids and then received sham transplants. Sham transplants (grafts) were carried out by lowering the graft injection needle to the appropriate site without making an injection.

The water maze consisted of a black polypropylene circular pool (2 m diameter, 0.5 m high, with 0.25 m depth of water at 26° C., rendered opaque with the addition of 200 ml milk). The escape platform was a 9cm clear perspex closed cylinder, located 0.02 m below the water surface in the middle of the North West quadrant of the pool. At the start of the trials, rats were placed in the pool facing the wall and allowed to swim until they found the platform, where they remained for 10 seconds before removal. A rat which failed to find a platform within 60 seconds was guided to it by the experimenter and the maximum latency scored. Start positions were designated as North, South, East or West and, in pseudorandom order, one start point close to the platform and one point distant from it were used each day. The swim path was recorded by an image analysing system (HVS Image, VP112), and digitally converted into a range of navigational measures.

The error bar indicates 2 standard errors between groups from the Groups X Days interaction of the analysis of variance. Latency to find the platform for the ischaemic rats with both CA1 and tsA58 grafts was not significantly different from unlesioned controls (sham-lesioned control rats which received sham grafts) (CON), whereas the other ischaemia groups with CA3 or sham grafts were significantly impaired relative to the control, CA1 and tsA58 groups in latency and other measures of spatial learning. Post-mortem analysis showed similar selective CA1 neuronal loss (70–75%) from host CA1 in all ischaemic groups including each of the grafted groups. Graft survival was excellent in all grafted groups.

Latency in the Morris water maze test is the time taken for a subject to swim to a hidden platform.

The results are shown in FIG. 9.

EXAMPLE 6

A clonal cell line (MHP36) derived from H-2K$^b$-tsA58 hippocampal precursor cells, restores spatial learning and memory in rats with ischaemic lesions of CA1.

The effects of grafts of cell suspensions of E19 CA1 (CA1), expanded cultures of E14 transgenic H-2K$^b$-tsA58 hippocampal neuroepithelial cells (tsA58) (harvested at Passage 5) and an expanded clonal cell line (MHP36) derived from E14 immortal hippocampal precursor population on acquisition of a hidden platform position in the Morris water maze following 15 minutes of 4VO ischaemia (ISC), producing lesions of CA1 were studied. Methods were as described in Example 5. MHP36 cells were removed from permissive culture and resuspended in Hank's balanced salt solution with 1 mM n-acetyl-L-cysteine ready for grafting.

As in Example 5, grafts were bilaterally targeted to the dorsal CA1 cell field (2 sites/hemisphere, 2 µl/site, 25K cells/µl for each cell-type graft) and graft surgery was conducted 7 to 14 days after ischaemia. All rats in this experiment (including ungrafted (sham-graft) and unlesioned (sham-lesioned) controls) were treated every other day for 14 days post-transplantation with the immunosuppressant, cyclosporin A (Sandoz, 2.5 mg/rat in Cremophore EL, i.m.). Training (2 trials/day) began 12 week post-transplantation (Ns=7–11/group). The error bar indicates 2 standard errors between groups from the Groups X Days interaction of the analysis of variance. Replicating our first experiment, latency to find the platform for the ischaemic rats with both CA1 and tsA58 grafts was not significantly different from sham-lesioned controls, which received sham grafts, (CON). Moreover, the MHP36 clonal cell line grafted group was also not significantly impaired compared to the control, CA1 and tsA58 groups. The results of these experiments are show in FIG. 10.

The experiments demonstrate that the transplanted precursor cells appear to respond to signals from the damaged brain by taking up a phenotype able to replace or compensate for the functional deficits to which the damage otherwise leads.

Further, analysis of variance (ANOVA) with repeated measures showed significant main effects of Groups ($F_{4,38}$=2.92, P<0.05), Blocks ($F_{5,896}$=36.50, P<0.001) and a significant Groups X Blocks linear coefficient interaction ($F_{4,896}$=3.23, P<0.02). t-Test comparisons between linear coefficients revealed that the ischaemic-sham transplant group had significantly impaired escape latency performance compared to the control and the three grafted groups (minimum $t_{38}$=2.29, P<0.05); the control and the three grafted groups did not significantly differ among themselves (all $t_{38}$<1). ANOVAs of swim distances revealed similar outcomes to the latency results.

EXAMPLE 7

The water maze tests of Examples 5 and 6 were repeated in a further set of experiments, see below. (In these experiments all rats were immunosupressed by intramuscular injection of cyclosporin-A (2.5 mg/rat in Cremophore EL) every other day for 15 days post-transplantation. The results are shown in FIG. 11. In that figure the mean time taken to find the platform is expressed as a function of two-day (4 trial) blocks of training. Bars show 2× s.e.m. from the Group X Blocks interaction of the analyses of variance.

These results further confirm that grafts of MHP36 cells are able to reverse ischaemia induced learning deficits. Both control (sham-lesioned rats which received sham grafts) and MHP36 groups showed significantly faster escape latencies and shorter swim distances to the escape platform than the group with ischaemia which received sham grafts.

An ischaemic group with grafts of MHP36 cells (P24–32) (N=12) (closed squares) was compared to ischaemic which received sham transplants (N=10) (closed circles) and sham-lesioned controls which received sham transplants (N=10) (open circles) on an identical water maze procedure. The ANOVA of escape latencies showed significant main effects of Groups ($F_{2,29}$=27.80, P<0.001), Blocks ($F_{5,674}$=54.72, P<0.001) and a significant Groups X Blocks interaction (F10.674=5.81, P<0.001), with a significant linear coefficient interaction ($F_{2,674}$=23.31, P<0.001). t-Test comparisons between linear coefficients revealed that the ischaemic-sham transplant group had significantly impaired escape latency performance compared to both the control and the MHP36 grafted groups (minimum $t_{29}$=5.54, P<0.001); the control and the MHP36 group were not significantly different ($t_{29}$=1.01). ANOVAs on swim distance and other measures of spatial learning in the water maze were entirely consistent with the escape latency results.

EXAMPLE 8

The experiments in Example 7 were repeated using grafts of cell from the MHP3 and MHP15 cell lines. MHP3 is one of the nine clonal cell lines mentioned in Example 2 above and is one of the cell lines which showed responsiveness to FGF2. The results are shown in FIG. 12. Also shown in that figure are results for control rats (again sham-lesioned rats which received sham grafts), ischaemic rats which received sham grafts and ischaemic rats which have received an implant of cells of the MHP36 cell line, as in Example 7 above. For MHP3 and MHP15 N=9. As may be seen, grafts of MHP3 cells produce as effective learning performance as those of MHP36, i.e., significantly faster than for the ischaemic group, but not significantly slower than for the control group. Grafts of MHP15 cells produce intermediate effects, i.e., significantly faster than for the ischaemic group, but also significantly slower than for the control group.

EXAMPLE 9

Post-mortem ischaemic brain damage in Experiment 7A was assessed from cresyl violet stained sections by two independent observers in cortex and striatum at two levels and in areas CA1–4 of the hippocampus at two further levels. Using a five-point scale, no damage was found in any region other than CA1, with the exception of two rats that showed mild CA3 cell loss. Independently of areas of grafted cells, average CA1 cell loss at the level of maximal ischaemic damage (inter-aural anterior 5.7 mm) ranged from 80% in the ischaemia plus sham transplant group to 90% in the ischaemia plus CA1 graft group, with no significant differences among the ischaemia alone (sham-graft) and ischaemia-plus-graft groups. Transplants of E19 fetal CA1 cells formed a circumscribed graft mass located above the CA1-damaged area, similar to those previously reported. $^3$H-thymidine-labelled expanded population cells were found dispersed throughout the entire hippocampal formation, the corpus callosum and the overlying neocortex; some clusters of labelled cells were found within the lesioned CA1 cell layer. Grafts of X-gal-positive MHP36 cells had a much more restricted distribution: other than adjacent to the needle track, labelled cells were shown to be confined to the hippocampus. This probably reflects both a greater sensitivity of the radioactive label, as well as a down-regulation of β-gal expression over the long survival time in these experiments. As pilot experiments had shown when grafts of MHP36 cells were made into unlesioned hippocampus, the X-gal-positive cells appeared to integrate into all CA (but not dentate gyrus) neuronal cell-body layers. (Discrete labelled cells were found in the hippocampal tissue and particularly in areas CA3 and 4.) However, unlike the case of grafts into unlesioned hippocampus, dense aggregations of X-gal-stained cells were additionally found within the ischaemic CA1 cell layer. The degree of engraftment varied between rats such that aggregations were in a small proportion of the CA1 field, or almost fully populated the lesioned field within a particular section, apparent on both X-gal- and niss1-stained sections. For example, some aggregations were found in the same hemisphere at different points along the rostro-caudal axis of the damaged CA1 layer. From this it is clear that cells of the MHP36 cell line have a propensity to aggregate in the lesioned CA1 neuronal layer.

A time-course study of the migration of labelled grafted MHP36 cells in ischaemic rats, using anti-B-gal immunohistochemistry to identify grafted cells has shown that migration to and aggregation at CA1 is complete by 4 weeks post-grafting.

REFERENCES

Dunnett & Bjorklund, 1994, Functional Neural Transplantation, Raven Press, New York
Jat P. S. et al., 1991, P.N.A.S. (USA) 88, p5096
Lindvall, O, 1994, in Dunnett & Bjorklund, op. cit.
Sinden J. D. et al. (1995) Beh. Brain Sci. 18, p10
Wilson, P. O. G., Barber, P. C., Hamid Q., A. Power, B. F., Dhillon A. P., Rode, J., Day, I. N. M., Thompson, R. J., and Polak J. M., Br. J. Exp. Pathol 69, p91–104 (1988).
Hoshimaiuaru, M., Ray, J., Sah, D. W. Y., Gage, F. H., PNAS USA, Vol.93, p1518–1523, (1996)

The present invention is not to be limited in scope by the Examples given above which are intended to illustrate the invention. Indeed, various modifications of the invention in addition to those shown and described herein will become apparent to those skilled in the art and are intended to fall within the scope of the appended claims.

The content of the above-mentioned literature references are hereby incorporated by reference.

We claim:

1. A method for treating brain damage in a mammal, said method comprising intracerebrally transplanting pluripotent, nestin-positive, neuroepithelial cells into the damaged part of the brain of said mammal, wherein said cells have been genetically modified to be conditionally immortal, wherein said cells are immortal prior to said transplanting and differentiate after said transplanting, and wherein said transplanting improves brain function of said mammal.

2. The method of claim 1, wherein the brain damage is in the hippocampus of said mammal.

3. The method of claim 1, wherein said pluripotent, nestin-positive, neuroepithelial cells are cells of a clonal cell line.

4. The method of claim 1, wherein said method further comprises culturing said pluripotent, nestin-positive, neuroepithelial cells in serum-free medium prior to said transplanting.

5. The method of claim 1, wherein the brain damage is the result of hypoxia.

6. The method of claim 1, wherein said mammal is a human.

7. The method of claim 1, wherein the brain damage causes a cognitive deficit, and wherein said transplanting improves cognitive function of said mammal.

8. The method of claim 1, wherein the genetic modification comprises transduction with a temperature-sensitive oncogene.

9. The method of claim 1, wherein the genetic modification comprises transduction with a temperature-sensitive simian virus 40 large T antigen gene.

10. The method of claim 1, wherein the genetic modification comprises transduction with a temperature-sensitive simian virus 40 large T antigen gene under the control of an interferon-inducible H-2K$^b$ promoter.

11. The method of claim 1, wherein said cells are immortal at 33° C. and differentiate at 39° C.

12. A method for treating brain damage in a mammal, said method comprising intracerebrally transplanting human pluripotent, nestin-positive, neuroepithelial cells into the damaged part of the brain of said mammal, wherein said human pluripotent, nestin-positive, neuroepithelial cells comprise a temperature-sensitive simian virus 40 large T antigen gene, and wherein said transplanting improves brain function of said mammal.

13. The method of claim 12, wherein said mammal is human.

14. The method of claim 12, wherein said cells are immortal at 33° C. and differentiate at 39° C.

15. The method of claim 12, wherein said temperature-sensitive simian virus 40 large T antigen gene is under the control of an interferon-inducible H-2K$^b$ promoter.

16. A method for treating brain damage in the hippocampus of a mammal, said method comprising intracerebrally transplanting human pluripotent, nestin-positive, neuroepithelial cells into the damaged hippocampus of said mammal, wherein said human pluripotent, nestin-positive, neuroepithelial cells comprise a temperature-sensitive simian virus 40 large T antigen gene, and wherein said transplanting improves cognitive function of said mammal.

17. The method of claim 16, wherein said mammal is human.

* * * * *